United States Patent
Hustvedt et al.

(10) Patent No.: US 11,612,579 B2
(45) Date of Patent: *Mar. 28, 2023

(54) COMPOSITIONS COMPRISING A FATTY ACID OIL MIXTURE AND A SURFACTANT, AND METHODS AND USES THEREOF

(75) Inventors: Svein Olaf Hustvedt, Oslo (NO); Preben Houlberg Olesen, Copenhagen (DK); Gunnar Berge, Oslo (NO); Jo Erik Johnsrud Klaveness, Oslo (NO)

(73) Assignee: PRONOVA BIOPHARMA NORGE AS, Lysaker (NO)

( * ) Notice: Subject to any disclaimer, the term of this patent is extended or adjusted under 35 U.S.C. 154(b) by 0 days.

This patent is subject to a terminal disclaimer.

(21) Appl. No.: 13/255,595

(22) PCT Filed: Mar. 9, 2010

(86) PCT No.: PCT/IB2010/000824
§ 371 (c)(1),
(2), (4) Date: May 4, 2012

(87) PCT Pub. No.: WO2010/103404
PCT Pub. Date: Sep. 16, 2010

(65) Prior Publication Data
US 2012/0225945 A1    Sep. 6, 2012

Related U.S. Application Data

(60) Provisional application No. 61/254,293, filed on Oct. 23, 2009, provisional application No. 61/254,291, filed on Oct. 23, 2009, provisional application No. 61/242,630, filed on Sep. 15, 2009, provisional application No. 61/158,613, filed on Mar. 9, 2009.

(51) Int. Cl.
| | | |
|---|---|---|
| A61K 31/232 | (2006.01) | |
| A61K 9/48 | (2006.01) | |
| A61K 31/557 | (2006.01) | |
| A23L 33/10 | (2016.01) | |
| A23L 33/115 | (2016.01) | |
| A61K 9/08 | (2006.01) | |
| A61K 31/202 | (2006.01) | |
| A61K 9/20 | (2006.01) | |
| A61K 31/201 | (2006.01) | |
| A61K 9/107 | (2006.01) | |

(52) U.S. Cl.
CPC ............ *A61K 31/232* (2013.01); *A23L 33/10* (2016.08); *A23L 33/115* (2016.08); *A61K 9/08* (2013.01); *A61K 9/20* (2013.01); *A61K 9/4825* (2013.01); *A61K 9/4858* (2013.01); *A61K 9/4866* (2013.01); *A61K 31/201* (2013.01); *A61K 31/202* (2013.01); *A61K 31/557* (2013.01); *A61K 9/1075* (2013.01)

(58) Field of Classification Search
CPC .................................................. A61K 31/232
See application file for complete search history.

(56) References Cited

U.S. PATENT DOCUMENTS

| | | | |
|---|---|---|---|
| 4,525,306 A * | 6/1985 | Yajima | A23D 9/06 |
| | | | 426/93 |
| 4,652,441 A | 3/1987 | Okada et al. | |
| 5,445,832 A | 8/1995 | Orsolini et al. | |
| 5,502,077 A | 3/1996 | Breivik et al. | |
| 5,532,002 A * | 7/1996 | Story | 424/456 |
| 5,645,856 A * | 7/1997 | Lacy et al. | 424/455 |
| 5,656,667 A | 8/1997 | Breivik et al. | |
| 5,698,594 A | 12/1997 | Breivik et al. | |
| 5,792,795 A | 8/1998 | Buser et al. | |
| 6,245,811 B1 | 6/2001 | Horrobin et al. | |
| 6,284,268 B1 | 9/2001 | Mishra et al. | |
| 6,689,812 B2 * | 2/2004 | Peet et al. | 514/560 |
| 7,560,486 B2 * | 7/2009 | Carpentier et al. | 514/560 |
| 9,370,493 B2 | 6/2016 | Klaveness et al. | |
| 2004/0254357 A1 | 12/2004 | Zaloga et al. | |
| 2005/0037065 A1 | 2/2005 | Kirschner et al. | |
| 2005/0118254 A1 * | 6/2005 | Choi et al. | 424/451 |
| 2006/0034815 A1 * | 2/2006 | Guzman et al. | 424/94.1 |

(Continued)

FOREIGN PATENT DOCUMENTS

| | | |
|---|---|---|
| CN | 101127049 A | 8/2007 |
| EP | 0052510 | 8/1986 |

(Continued)

OTHER PUBLICATIONS

Welch, A. et al., Dietary intake and status of n23 polyunsaturated fatty acids in a population of fish-eating and non-fish-eating meat-eaters, vegetarians, and vegans and the precursor-product ratio of a-linolenic acid to long-chain n23 polyunsaturated fatty acids: results from the EPIC-Norfolk cohort. Am J Clin Nutr 2010;92:1040-51.*
Rustan and Drevon in "Fatty Acids: structures and properties" p. 1, col. 2, Encyclopedia of Life Sciences 2005, John Wiley & Sons, Ltd. www.els.net.*
Sears, Understanding Eicosanoids, (http://www.drsears.com/ArticlePreview/tabid/399/itemid/66/Default.aspx).*
Uson, N. et al., Formation of water-in-oil (W/O) nano-emulsions in a water/mixed non-ionic surfactant/oil systems prepared by a low-energy emulsification method, Colloids and Surfaces A: Physicochem. Eng. Aspects 250 (2004) 415-421.*

(Continued)

Primary Examiner — Yong S. Chong
(74) Attorney, Agent, or Firm — Finnegan, Henderson, Farabow, Garrett & Dunner, LLP

(57) ABSTRACT

A preconcentrate comprising a fatty acid oil mixture that contains EPA and DHA, preferably in the form of ethyl ester or triglyceride, and at least one surfactant. The preconcentrates are capable of forming a self-nanoemulsifying drug delivery system, a self-microemulsifying drug delivery system or a self-emulsifying drug delivery system (SNEDDS, SMEDDS or SEDDS) in an aqueous solution. The application is also directed to a food supplement preconcentrate.

119 Claims, 9 Drawing Sheets

(56) References Cited

U.S. PATENT DOCUMENTS

| | | |
|---|---|---|
| 2006/0211763 A1 | 9/2006 | Fawzy et al. |
| 2007/0021504 A1 | 1/2007 | Yokoyama et al. |
| 2007/0141138 A1 | 6/2007 | Feuerstein et al. |
| 2008/0261896 A1* | 10/2008 | Tanaka et al. ............ 514/25 |
| 2009/0011012 A1 | 1/2009 | Baum |
| 2009/0030077 A1* | 1/2009 | Almarsson et al. ......... 514/543 |
| 2009/0137556 A1* | 5/2009 | Bonnichsen ............ 514/212.07 |
| 2010/0112047 A1 | 5/2010 | Feuerstein et al. |
| 2010/0130608 A1 | 5/2010 | Ryan et al. |
| 2010/0160435 A1* | 6/2010 | Bruzzese ............ 514/560 |
| 2010/0285121 A1 | 11/2010 | Uchiyama et al. |
| 2011/0262534 A1 | 10/2011 | Berge et al. |
| 2012/0207800 A1 | 8/2012 | Abu-Baker et al. |
| 2013/0108696 A1 | 5/2013 | Berge et al. |

FOREIGN PATENT DOCUMENTS

| | | |
|---|---|---|
| EP | 0346879 | 12/1989 |
| EP | 1157692 | 11/2001 |
| EP | 2124973 | 12/2009 |
| ES | 2009346 | 9/1989 |
| GB | 1393805 | 5/1975 |
| GB | 2033745 | 5/1980 |
| GB | 2209937 | 6/1988 |
| GB | 2388026 | 11/2003 |
| JP | H04507418 | 12/1992 |
| JP | H0889167 | 4/1996 |
| JP | 1999-509523 | 8/1999 |
| JP | 2009-525992 | 7/2009 |
| WO | WO 1991/002520 | 3/1991 |
| WO | WO9102520 A1 | 3/1991 |
| WO | WO 1996/036329 | 11/1996 |
| WO | WO 99/29316 | 6/1999 |
| WO | WO 1999/029300 | 6/1999 |
| WO | WO 1999/029335 | 6/1999 |
| WO | WO 99/56727 | 11/1999 |
| WO | WO 03/068216 | 8/2003 |
| WO | WO 2004/047835 | 6/2004 |
| WO | WO 2004/056370 | 7/2004 |
| WO | WO 2005/123060 | 12/2005 |
| WO | WO 2005/123061 | 12/2005 |
| WO | WO 2006/024237 | 3/2006 |
| WO | WO 2007/075841 | 7/2007 |
| WO | WO 2007/090408 | 8/2007 |
| WO | WO 2008/002121 | 1/2008 |
| WO | WO 2008/011179 A2 | 1/2008 |
| WO | WO 2008/088415 A1 | 7/2008 |
| WO | WO 2009/009040 | 1/2009 |
| WO | WO 2009/087939 | 7/2009 |

OTHER PUBLICATIONS

The European Agency for the Evaulation of Medicinal Products Jun. 1999. http://www.ema.europa.eu/docs/en_GB/document_library/Maximum_Residue_Limits_-_Report/2009/11/WC500015765.pdf.*

Eastwood, Jennifer et al., Who Food Additives Series 48—Safety Evaluation of Certain Food Additives and Contaminants (2001)—http://www.inchem.org/documents/jecfa/jecmono/v48je03.htm.*

Ensminger, et al., Foods & Nutrition Encyclopedia, $2^{nd}$ Edition, vol. 1. p. 688, Fats and Other Lipds.*

Harwood, J. L., Ann. Rev. Plant Physiol. Plant Mol. Biol. 1988, 39: 101-38, Fatty Acid Metabolism; http://www.annualreviews.org/doi/pdf/10.1146/annurev.pp.39.060188.000533.*

International Search Report of International Patent Application No. PCT/IB2010/000824, dated Jun. 28, 2010.

International Preliminary Report on Patentability of International Patent Application No. PCT/IB2010/000824, dated Sep. 13, 2011.

Ratanabanangkoon et al., "A high-throughput approach towards a novel formulation of fenofibrate in omega-3 oil," European Journal of Pharmaceutical Sciences, vol. 33, pp. 351-360 (2008).

Hiroshi Nishino et al., Effects of various additives on the solution properties of middle phase microemulsion with nonionic surfactants, Journal of the Japan Petroleum Institute, published in 1990, vol. 33, No. 4, pp. 234-240.

Alaska Alaskan Omega-3 EPA DHA—180 Softgels, Product Description, available at https://www.amazon.com/Clinical-Strength-Concentrated-Alaskan-Softgels/dp/B005NWKP0A/ref=sr_1_3_a_it?ie=UTF8&qid=1481735194&sr=8-&keywords=Pure+Alaska+Alaskan+Omega-3+fish+oil (last accessed Sep. 22, 2017).

Tsikas et al., "Analysis of eicosanoids by LC-MS/MS and GC-MS/MS: A historical retrospect and a discussion," J. Chromatography B, vol. 964, pp. 79-88 (2014).

Zangenberg et al., "A Dynamic in Vitro Lipolysis Model: Controlling the Rate of Lipolysis by Continuous Addition of Calcium," Eur. J. Pharm. Sci., vol. 14, No. 2, pp. 115-122 (2001).

Zangenberg et al., "A Dynamic in Vitro Lipolysis Model: Evaluation of the Model," Eur. J. Pharm. Sci., vol. 14, No. 3, pp. 237-244 (2001).

* cited by examiner

COMPOSITIONS COMPRISING A FATTY ACID OIL MIXTURE AND A SURFACTANT, AND METHODS AND USES THEREOF

This application is a National Phase application based on International Patent Application No. PCT/IB2010/000824 filed on Mar. 9, 2010, and claims priority to U.S. Provisional Application No. 61/158,613, filed on Mar. 9, 2009, U.S. Provisional Application No. 61/242,630, filed on Sep. 15, 2009, U.S. Provisional Application No. 61/254,291, filed on Oct. 23, 2009, and U.S. Provisional Application No. 61/254,293, filed on Oct. 23, 2009, all of which are incorporated herein by reference in their entireties.

The present disclosure relates generally to preconcentrates comprising a fatty acid oil mixture and at least one surfactant, and methods of use thereof. The fatty acid oil mixture may comprise omega-3 fatty acids, such as eicosapentaenoic acid (EPA) and docosahexaenoic acid (DHA) in ethyl ester or triglyceride form. Further disclosed are self-nanoemulsifying drug delivery systems (SNEDDS), self-microemulsifying drug delivery systems (SMEDDS) and self-emulsifying drug delivery systems (SEDDS).

The preconcentrates presently disclosed may be administered, e.g., in capsule form, to a subject for therapeutic treatment and/or regulation of at least one health problem including, for example, irregular plasma lipid levels, cardiovascular functions, immune functions, visual functions, insulin action, neuronal development, hypertriglyceridemia, heart failure, and post myocardial infarction (MI). The present disclosure further relates to a method of increasing hydrolysis, solubility, bioavailability, absorption, and/or any combination thereof.

In humans, cholesterol and triglycerides are part of lipoprotein complexes in the bloodstream and can be separated via ultracentrifugation into high-density lipoprotein (HDL), intermediate-density lipoprotein (IDL), low-density lipoprotein (LDL), and very-low-density lipoprotein (VLDL) fractions. Cholesterol and triglycerides are synthesized in the liver, incorporated into VLDL, and released into the plasma. High levels of total cholesterol (total-C), LDL-C, and apolipoprotein B (a membrane complex for LDL-C and VLDL-C) promote human atherosclerosis and decreased levels of HDL-C and its transport complex; apolipoprotein A is also associated with the development of atherosclerosis. Furthermore, cardiovascular morbidity and mortality in humans can vary directly with the level of total-C and LDL-C and inversely with the level of HDL-C. In addition, research suggests that non-HDL cholesterol is an indicator of hypertriglyceridemia, vascular disease, atherosclerotic disease, and related conditions. In fact, NCEP ATP III specifies non-HDL cholesterol reduction as a treatment objective.

Omega-3 fatty acids may regulate plasma lipid levels, cardiovascular and immune functions, insulin action, and neuronal development, and visual function. Marine oils, also commonly referred to as fish oils, are a source of omega-3 fatty acids, including eicosapentaenoic acid (EPA) and docosahexaenoic acid (DHA), have been found to regulate lipid metabolism. Plant-based oils and microbial oils are also sources of omega-3 fatty acids. Omega-3 fatty acids may have beneficial effects on the risk factors for cardiovascular diseases, for example hypertension and hypertriglyceridemia, and on the coagulation factor VII phospholipid complex activity. Omega-3 fatty acids may also lower serum triglycerides, increase serum HDL cholesterol, lower systolic and diastolic blood pressure and/or pulse rate, and may lower the activity of the blood coagulation factor VII-phospholipid complex. Further, omega-3 fatty acids are generally well-tolerated, without giving rise to severe side effects.

Several formulations of omega-3 fatty acids have been developed. For example, one form of omega-3 fatty acid oil mixture is a concentrate of primary omega-3, long chain, polyunsaturated fatty acids from fish oil containing DHA and EPA, such as sold under the trademark Omacor®/Lovaza™/Zodin®/Seacor®. See, for example, U.S. Pat. Nos. 5,502,077, 5,656,667 and 5,698,594. In particular, each 1000 mg capsule of Lovaza™ contains at least 90% omega-3 ethyl ester fatty acids (84% EPA/DHA); approximately 465 mg EPA ethyl ester and approximately 375 mg DHA ethyl ester.

Further, for example, EPA/DHA ethyl esters have also been used in compositions for delivery of therapeutic drugs. For instance, U.S. Pat. No. 6,284,268 (Cyclosporine Therapeutics Ltd.) describes a self-emulsifying microemulsion or emulsion preconcentrate pharmaceutical compositions containing an omega-3 fatty acid oil and poorly water soluble therapeutic agent such as cyclosporine for oral administration. Cyclosporines are claimed to have additive or synergistic therapeutic effects with omega-3 fatty acid oil. The '268 patent discloses greater solubility and stability of cyclosporine formulations comprising omega-3 fatty acid oils. WO 99/29300 (RTP Pharma) relates to self-emulsifying fenofibrate formulations based on a hydrophobic component selected from triglyceride, diglyceride, monoglycerides, free fatty acids and fatty acids and derivatives thereof.

However, evidence suggests that long chain fatty acids and alcohols of up to at least $C_{24}$ are reversibly interconverted. Enzyme systems exist in the liver, fibroblasts, and the brain that convert fatty alcohols to fatty acids. In some tissues, fatty acids can be reduced back to alcohols. The carboxylic acid functional group of fatty acid molecules targets binding, but this ionizable group may hinder the molecule from crossing the cell membranes, such as of the intestinal wall. As a result, carboxylic acid functional groups are often protected as esters. The ester is less polar than the carboxylic acid, and may more easily cross the fatty cell membranes. Once in the bloodstream, the ester can be hydrolyzed back to the free carboxylic acid by enzyme esterase in the blood. It may be possible that the plasma enzymes do not hydrolyze the ester fast enough, however, and that the conversion of ester to free carboxylic acid predominantly takes place in the liver. Ethyl esters of polyunsaturated fatty can also be hydrolyzed to free carboxylic acids in vivo.

Thus, there remains a need in the art for compositions and/or methods that improve or enhance solubilization, digestion, bioavailability and/or absorption of omega-3 fatty acids in vivo, while maintaining the ability to cross cell membranes.

It is to be understood that both the foregoing general description and the following detailed description are exemplary and explanatory only and are not restrictive of the present disclosure, as claimed.

The present disclosure is further directed to a pharmaceutical preconcentrate comprising: a fatty acid oil mixture comprising at least 75% eicosapentaenoic acid (EPA) and docosahexaenoic acid (DHA), by weight of the fatty acid oil mixture, wherein the EPA and DHA are in a form chosen from ethyl ester and triglyceride; and at least one surfactant.

The present disclosure is further directed to a pharmaceutical preconcentrate comprising: a fatty acid oil mixture comprising from about 80% to about 88% eicosapentaenoic acid (EPA) and docosahexaenoic acid (DHA), by weight of the fatty acid oil mixture, wherein the EPA and DHA are in ethyl ester form; and at least one surfactant chosen from polysorbate 20, polysorbate 80, and mixtures thereof.

The present disclosure is further directed to a pharmaceutical preconcentrate comprising: a fatty acid oil mixture comprising from about 80% to about 88% eicosapentaenoic acid (EPA) and docosahexaenoic acid (DHA), by weight of the fatty acid oil mixture, wherein the EPA and DHA are in ethyl ester form; at least one surfactant chosen from polysorbate 20, polysorbate 80, and mixtures thereof; and at least one co-surfactant comprising ethanol.

The present disclosure is further directed to a self-nanoemulsifying drug delivery system (SNEDDS), self-microemulsifying drug delivery system (SMEDDS), or self-emulsifying drug delivery system (SEDDS) comprising a pharmaceutical preconcentrate comprising: a fatty acid oil mixture comprising from about 80% to about 88% eicosapentaenoic acid (EPA) and docosahexaenoic acid (DHA), by weight of the fatty acid oil mixture, wherein the EPA and DHA are in a form chosen from ethyl ester and triglyceride; and at least one surfactant; wherein the preconcentrate forms an emulsion in an aqueous solution.

The present disclosure is further directed to a method of treating at least one health problem in a subject in need thereof comprising administering to the subject a pharmaceutical preconcentrate comprising: a fatty acid oil mixture comprising at least 75% eicosapentaenoic acid (EPA) and docosahexaenoic acid (DHA), by weight of the fatty acid oil mixture, wherein the EPA and DHA are in a form chosen from ethyl ester and triglyceride; and at least one surfactant; wherein the at least one health problem is chosen from irregular plasma lipid levels, cardiovascular functions, immune functions, visual functions, insulin action, neuronal development, heart failure, and post myocardial infarction.

The present disclosure is further directed to a food supplement preconcentrate or nutritional supplement preconcentrate comprising: a fatty acid oil mixture comprising from about 25% to about 75% eicosapentaenoic acid (EPA) and docosahexaenoic acid (DHA), by weight of the fatty acid oil mixture, wherein the EPA and DHA are in a form chosen from ethyl ester and triglyceride; and at least one surfactant.

The present disclosure is further directed to a method for enhancing at least one parameter chosen from hydrolysis, solubility, bioavailability, absorption, and combinations thereof of eicosapentaenoic acid (EPA) and docosahexaenoic acid (DHA) comprising combining: a fatty acid oil mixture comprising EPA and DHA in a form chosen from ethyl ester and triglyceride; and at least one surfactant; wherein the fatty acid oil mixture and the at least one surfactant form a preconcentrate.

The present disclosure is further directed to a method of regulating at least one health problem in a subject in need thereof comprising administering to the subject a supplement preconcentrate comprising: a fatty acid oil mixture comprising from about 25% to about 75% eicosapentaenoic acid (EPA) and docosahexaenoic acid (DHA), by weight of the fatty acid oil mixture, wherein the EPA and DHA are in a form chosen from ethyl ester and triglyceride; and at least one surfactant; wherein the at least one health problem is chosen from irregular plasma lipid levels, cardiovascular functions, immune functions, visual functions, insulin action, neuronal development, heart failure, and post myocardial infarction.

The present disclosure is further directed to a food supplement or nutritional supplement preconcentrate comprising: a fatty acid oil mixture comprising from about 25% to about 75% eicosapentaenoic acid (EPA) and docosahexaenoic acid (DHA), by weight of the fatty acid oil mixture, wherein the EPA and DHA are in a form chosen from ethyl ester and triglyceride; and at least one surfactant for the regulation of at least one health problem chosen from irregular plasma lipid levels, cardiovascular functions, immune functions, visual functions, insulin action, neuronal development, heart failure, and post myocardial infarction.

DESCRIPTION

Figure 1:
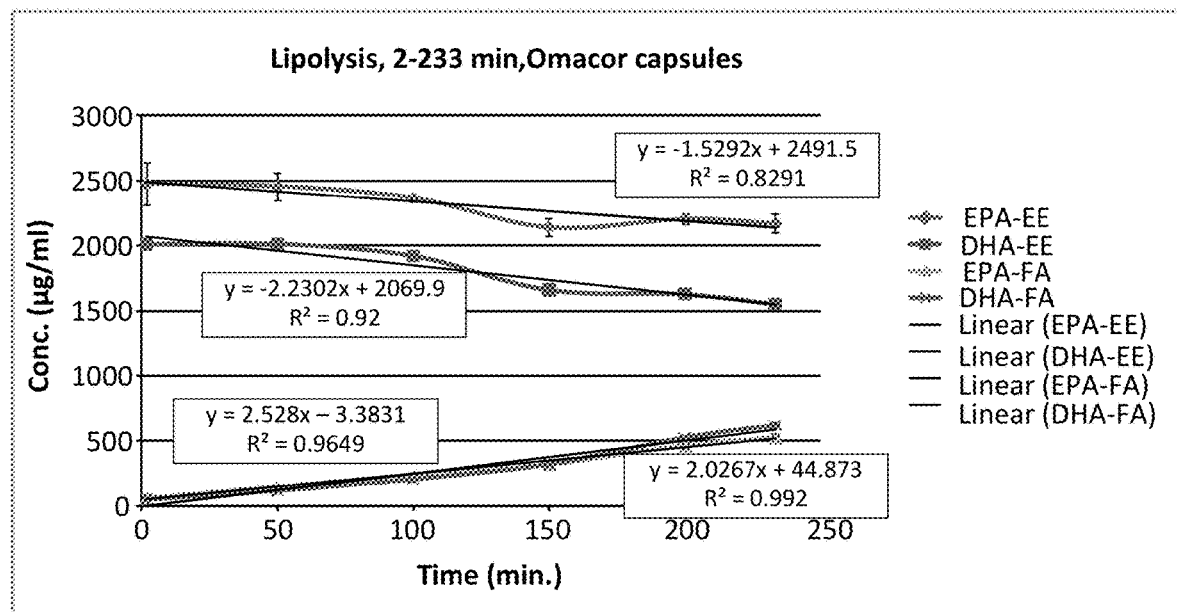
FIG. 1 shows the disappearance of EPA-EE and DHA-EE and the appearance of EPA-FA and DHA-FA during lipolysis of Omacor®.

Particular aspects of the disclosure are described in greater detail below. The terms and definitions as used in the present application and as clarified herein are intended to represent the meaning within the present disclosure. The patent and scientific literature referred to herein and referenced above is hereby incorporated by reference. The terms and definitions provided herein control, if in conflict with terms and/or definitions incorporated by reference.

The singular forms "a," "an," and "the" include plural reference unless the context dictates otherwise.

The terms "approximately" and "about" mean to be nearly the same as a referenced number or value. As used herein, the terms "approximately" and "about" should be generally understood to encompass±10% of a specified amount, frequency or value.

The terms "administer," "administration" or "administering" as used herein refer to (1) providing, giving, dosing and/or prescribing by either a health practitioner or his authorized agent or under his direction a preconcentrate according to the disclosure, and (2) putting into, taking or consuming by the patient or person himself or herself, a preconcentrate according to the disclosure.

The present disclosure provides for pharmaceutical and supplement preconcentrates comprising a fatty acid oil mixture and at least one surfactant, and methods of use thereof. The preconcentrates of the present disclosure can produce dispersions of low or very low mean particle size when mixed with an aqueous medium. Such dispersions can be characterized as nanoemulsions, microemulsions, or emulsions. For example, upon delivery, the preconcentrates are thought to produce dispersions with gastric or other physiological fluids generating self-nanoemulsifying drug delivery systems (SNEDDS), self-microemulsifying drug delivery systems (SMEDDS), or self emulsifying drug delivery systems (SEDDS).

Fatty Acid Oil Mixture

Compositions of the present disclosure comprise at least one fatty acid oil mixture comprising eicosapentaenoic acid (EPA) and docosahexaenoic acid (DHA). As used herein, the term "fatty acid oil mixture" includes fatty acids, such as unsaturated (e.g., monounsaturated, polyunsaturated) or saturated fatty acids, as well as pharmaceutically-acceptable esters, free acids, mono-, di- and triglycerides, derivatives, conjugates, precursors, salts, and mixtures thereof. In at least one embodiment, the fatty acid oil mixture comprises fatty acids, such as omega-3 fatty acids, in a form chosen from ethyl ester and triglyceride.

The term "omega-3 fatty acids" includes natural and synthetic omega-3 fatty acids, as well as pharmaceutically-acceptable esters, free acids, triglycerides, derivatives, conjugates (see, e.g., Zaloga et al., U.S. Patent Application Publication No. 2004/0254357, and Horrobin et al., U.S. Pat. No. 6,245,811, each hereby incorporated by reference), precursors, salts, and mixtures thereof. Examples of omega-3 fatty acid oils include, but are not limited to, omega-3 polyunsaturated, long-chain fatty acids such as eicosapentaenoic acid (EPA), docosahexaenoic acid (DHA), α-linolenic acid (ALA), heneicosapentaenoic acid (HPA), docosapentaenoic acid (DPA), eicosatetraenoic acid (ETA), eicosatrienoic acid (ETE), and octadecatetraenoic acid (i.e., stearidonic acid, STA); esters of omega-3 fatty acids with glycerol such as mono-, di- and triglycerides; and esters of the omega-3 fatty acids and a primary, secondary and/or tertiary alcohol, such as, for example, fatty acid methyl esters and fatty acid ethyl esters. The omega-3 fatty acids, esters, triglycerides, derivatives, conjugates, precursors, salts and/or mixtures thereof according to the present disclosure can be used in their pure form and/or as a component of an oil, for example, as marine oil (e.g., fish oil and purified fish oil concentrates), algae oils, microbial oils and plant-based oils.

In some embodiments of the present disclosure, the fatty acid oil mixture comprises EPA and DHA. Further for example, the fatty acid oil mixture comprises EPA and DHA in a form chosen from ethyl ester and triglyceride.

The fatty acid oil mixture of the present disclosure may further comprise at least one fatty acid other than EPA and DHA. Examples of such fatty acids include, but are not limited to, omega-3 fatty acids other than EPA and DHA and omega-6 fatty acids. For example, in some embodiments of the present disclosure, the fatty acid oil mixture comprises at least one fatty acid other than EPA and DHA chosen from α-linolenic acid (ALA), heneicosapentaenoic acid (HPA), docosapentaenoic acid (DPA), eicosatetraenoic acid (ETA), eicosatrienoic acid (ETE), and stearidonic acid (STA). In some embodiments, the at least one fatty acid other than EPA and DHA is chosen from linoleic acid, gamma-linolenic acid (GLA), arachidonic acid (AA), docosapentaenoic acid (i.e., osbond acid), and mixtures thereof. In some embodiments, the at least one fatty acid other than EPA and DHA is in a form chosen from ethyl ester and triglyceride.

Examples of further fatty acids, or mixtures thereof (fatty acid oil mixtures) encompassed by the present disclosure include, but are not limited to, the fatty acids defined in the European Pharamacopoeia Omega-3 Ethyl Esters 90 and purified marine oils, the European Pharamacopoeia Omega-3 Acid Triglycerides, the European Pharamacopoeia Omega-3 acid Ethyl Esters 60, the European Pharamacopoeia Fish Oil Rich in Omega-3 Acids monograph, and/or for instance, the USP fish oil monograph.

Commercial examples of fatty acid oil mixtures comprising different fatty acids suitable for the present disclosure include, but are not limited to: Incromega™ omega-3 marine oil concentrates such as Incromega™ TG7010 SR, Incromega™ E7010 SR, Incromega™ TG6015, Incromega™ EPA500TG SR, Incromega™ E400200 SR, Incromega™ E4010, Incromega™ DHA700TG SR, Incromega™ DHA700E SR, Incromega™ DHA500TG SR, Incromega™ TG3322 SR, Incromega™ E3322 SR, Incromega™ TG3322, Incromega™ E3322, Incromega™ Trio TG/EE (Croda International PLC, Yorkshire, England); EPAX6000FA, EPAX5000TG, EPAX4510TG, EPAX2050TG, EPAX7010EE, EPAX5500EE, EPAX5500TG, EPAX5000EE, EPAX5000TG, EPAX6000EE, EPAX6000TG, EPAX6000FA, EPAX6500EE, EPAX6500TG, EPAX4510TG, EPAX1050TG, EPAX2050TG, EPAX 7010TG, EPAX7010EE, EPAX6015TG/EE, EPAX4020TG, and EPAX4020EE (EPAX is a wholly-owned subsidiary of Norwegian company Austevoll Seafood ASA); Omacor®/Lovaza™/Zodin®/Seacor® finished pharmaceutical product, K85EE, and AGP 103 (Pronova BioPharma Norge AS); MEG-3® EPA/DHA fish oil concentrates (Ocean Nutrition Canada); DHA FNO "Functional Nutritional Oil" and DHA CL "Clear Liquid" (Lonza); Superba™ Krill Oil (Aker); omega-3 products comprising DHA produced by Martek; Neptune krill oil (Neptune); cod-liver oil products and anti-reflux fish oil concentrate (TG) produced by Møllers; Lysi Omega-3 Fish oil; Seven Seas Triomega® Cod Liver Oil Blend (Seven Seas); Fri Flyt Omega-3 (Vesterålens); and Epadel (Mochida). Those commercial embodiments provide for various omega-3 fatty acids, combinations, and other components as a result of the transesterification process or method of preparation in order to obtain the omega-3 fatty acid(s) from various sources, such as marine, algae, microbial, and plant-based sources.

In some embodiments of the present disclosure, the fatty acid oil mixture comprises at least one fatty acid derivative, such as an alpha-substituted omega-3 fatty acid derivative. The at least one alpha substituted omega-3 fatty acid derivative may be substituted, for example, at the second carbon atom from the functional group of the omega-3 fatty acid with at least one substituent chosen from hydrogen, hydroxyl groups, alkyl groups, such as $C_1$-$C_3$ alkyl groups, and alkoxy groups. In one embodiment of the present disclosure, the at least one alpha-substituted omega-3 fatty acid derivative is chosen from mono-substituted and di-substituted fatty acids. In one embodiment, the at least one alpha substituted omega-3 fatty acid derivative is chosen from alpha-substituted $C_{14}$-$C_{24}$ alkenes having 2 to 6 double bonds. In another embodiment, the at least one alpha-substituted omega-3 fatty acid derivative is chosen from alpha-substituted $C_{14}$-$C_{24}$ alkenes having 5 or 6 double bonds in cis configuration.

In some embodiments, the fatty acid oil mixture comprises EPA and/or DHA in a form of an alpha-substituted fatty acid derivative. For example, in one embodiment, the fatty acid oil mixture comprises EPA in a form of an alpha-substituted derivative. In another embodiment, the fatty acid oil mixture comprises DHA in a form of an alpha-substituted derivative. In yet another embodiment, the fatty acid oil mixture comprises EPA and DHA in a form of an alpha-substituted derivative.

In some embodiments, the fatty acid oil mixture comprises EPA and DHA, and further comprises at least one alpha-substituted omega-3 fatty acid derivative. For example, in some embodiments, the fatty acid oil mixture comprises EPA and DHA, and at least one of EPA and DHA in a form of an alpha-substituted derivative.

In another embodiment, the EPA and DHA of the fatty acid oil mixture is at least one alpha-substituted omega-3 fatty acid derivative.

The fatty acid oil mixture according to the present disclosure may be derived from animal oils and/or non-animal oils. In some embodiments of the present disclosure, the fatty acid oil mixture is derived from at least one oil chosen from marine oil, algae oil, plant-based oil, and microbial oil. Marine oils include, for example, fish oil, krill oil, and lipid composition derived from fish. Plant-based oils include, for example, flaxseed oil, canola oil, mustard seed oil, and soybean oil. Microbial oils include, for example, products by Martek. In at least one embodiment of the present disclosure, the fatty acid oil mixture is derived from a marine oil, such as a fish oil. In at least one embodiment, the marine oil is a purified fish oil.

In some embodiments of the present disclosure, the fatty acids, such as omega-3 fatty acids, of the fatty acid oil mixture are esterified, such as alkyl esters, such as ethyl ester. In other embodiments, the fatty acids are chosen from mono-, di-, and triglycerides.

In some embodiments, the fatty acid oil mixture is obtained by a transesterification of the body oil of a fat fish species coming from, for example, anchovy or tuna oil, and subsequent physico-chemical purification processes, including urea fractionation followed by molecular distillation. In some embodiments, the crude oil mixture may also be subjected to a stripping process for decreasing the amount of environmental pollutants and/or cholesterol before the transesterification.

In another embodiment, the fatty acid oil mixture is obtained by using supercritical $CO_2$ extraction or chromatography techniques, for example to up-concentrate primary EPA and DHA from fish oil concentrates.

In some embodiments of the present disclosure, at least one of the omega-3 fatty acids of the fatty acid oil mixture has a cis configuration. Examples include, but are not limited to, (all-Z)-9,12,15-octadecatrienoic acid (ALA), (all-Z)-6,9,12,15-octadecatetraenoic acid (STA), (all-Z)-11,14,17-eicosatrienoic acid (ETE), (all-Z)-5,8,11,14,17-eicosapentaenoic acid (EPA), (all-Z)-4,7,10,13,16,19-docosahexaenoic acid (DHA), (all-Z)-8,11,14,17-eicosatetraenoic acid (ETA), (all-Z)-7,10,13,16,19-docosapentaenoic acid (DPA), (all-Z)-6,9,12,15,19-heneicosapentaenoic acid (HPA); (all-Z)-5,8,11,14-eicosatetraenoic acid, (all-Z)-4,7,10,13,16-docosapentaenoic acid (osbond acid), (all-Z)-9,12-octadecadienoic acid (linoleic acid), (all-Z)-5,8,11,14-eicosatetraenoic acid (AA), (all-Z)-6,9,12-octadecatrienoic acid (GLA); (Z)-9-octadecenoic acid (oleic acid), 13(Z)-docosenoic acid (erucic acid), (R—(Z))-12-hydroxy-9-octadecenoic acid (ricinoleic acid).

In some embodiments of the present disclosure, the weight ratio of EPA:DHA of the fatty acid oil mixture ranges from about 1:10 to about 10:1, from about 1:8 to about 8:1, from about 1:6 to about 6:1, from about 1:5 to about 5:1, from about 1:4 to about 4:1, from about 1:3 to about 3:1, or from about 1:2 to about 2:1. In at least one embodiment, the weight ratio of EPA:DHA of the fatty acid oil mixture ranges from about 1:2 to about 2:1. In at least one embodiment, the weight ratio of EPA:DHA of the fatty acid oil mixture ranges from about 1:1 to about 2:1. In at least one embodiment, the weight ratio of EPA:DHA of the fatty acid oil mixture ranges from about 1:2 to about 1:3.

Pharmaceutical

In some embodiments of the present disclosure, the fatty acid oil mixture acts as an active pharmaceutical ingredient (API). For example, the present disclosure provides for a pharmaceutical composition comprising a fatty acid oil mixture and at least one surfactant. In some embodiments, the fatty acid oil mixture is present in a pharmaceutically-acceptable amount. As used herein, the term "pharmaceutically-effective amount" means an amount sufficient to treat, e.g., reduce and/or alleviate the effects, symptoms, etc., at least one health problem in a subject in need thereof. In at least some embodiments of the present disclosure, the fatty acid oil mixture does not comprise an additional active agent.

Where the preconcentrate is a pharmaceutical preconcentrate, the fatty acid oil mixture comprises at least 75% EPA and DHA by weight of the fatty acid oil mixture. In some embodiments, the fatty acid oil mixture comprises at least 80% EPA and DHA by weight of the fatty acid oil mixture, such as at least 85%, at least 90%, or at least 95%, by weight of the fatty acid oil mixture. In some embodiments, the fatty acid oil mixture comprises about 80% EPA and DHA by weight of the fatty acid oil mixture, such as about 85%, about 90%, about 95%, or any number in between, by weight of the fatty acid oil mixture.

For example, in some embodiments, the fatty acid oil mixture comprises from about 75% to about 95% EPA and DHA by weight of the fatty acid oil mixture, such as from about 75% to about 90%, from about 75% to about 88%, from about 75% to about 85%, from about 75% to about 80%, from about 80% to about 95%, from about 80% to about 90%, from about 80% to about 85%, from about 85% to about 95%, from about 85% to about 90%, and further for example, from about 90% to about 95% EPA and DHA, by weight of the fatty acid oil mixture, or any number in between. In at least one embodiment, the fatty acid oil mixture comprises from about 80% to about 85% EPA and DHA, by weight of the fatty acid oil mixture, such as from about 80% to about 88%, such as about 84%, by weight of the fatty acid oil mixture.

In some embodiments, the fatty acid oil mixture comprises at least 95% of EPA or DHA, or EPA and DHA, by weight of the fatty acid oil mixture, wherein the EPA and DHA are in ethyl ester form.

In a further embodiment, the fatty acid oil mixture may comprise other omega-3 fatty acids. For example, the present disclosure encompasses at least 90% omega-3 fatty acids, by weight of the fatty acid oil mixture.

In one embodiment, for example, the fatty acid oil mixture comprises from about 75% to about 88% EPA and DHA, by weight of the fatty acid oil mixture, wherein the EPA and DHA are in ethyl ester form; wherein the fatty acid oil mixture comprises at least 90% of omega-3 fatty acids in ethyl ester form, by weight of the fatty acid oil mixture.

In another embodiment, the fatty acid oil mixture comprises from about 75% to about 88% EPA and DHA, by weight of the fatty acid oil mixture, wherein the EPA and DHA are in ethyl ester form; wherein the fatty acid oil mixture comprises at least 90% of omega-3 fatty acids in ethyl ester form, by weight of the fatty acid oil mixture, and wherein the fatty acid oil mixture comprises α-linolenic acid (ALA).

In one embodiment, the fatty acid oil mixture comprises from about 80% to about 88% EPA and DHA by weight of the fatty acid oil mixture, wherein the EPA and DHA are in ethyl ester form, and further comprises docosapentaenoic acid (DPA) in ethyl ester form.

In another embodiment, the fatty acid oil mixture comprises from about 80% to about 88% EPA and DHA by weight of the fatty acid oil mixture, wherein the EPA and DHA are in ethyl ester form, and further comprises from about 1% to about 4% (all-Z omega-3)-6,9,12,15,18-heneicosapentaenoic acid (HPA) in ethyl ester form, by weight of the fatty acid oil mixture.

In another embodiment, the fatty acid oil mixture comprises from about 80% to about 88% EPA and DHA by weight of the fatty acid oil mixture, wherein the EPA and DHA are in ethyl ester form; and from 1% to about 4% fatty acid ethyl esters other than EPA and DHA, by weight of the fatty acid oil mixture, wherein the fatty acid ethyl esters other than EPA and DHA have $C_{20}$, $C_{21}$, or $C_{22}$ carbon atoms.

In one embodiment, the fatty acid oil mixture may comprise K85EE or AGP 103 (Pronova BioPharma Norge AS). In another embodiment, the fatty acid oil mixture may comprise K85TG (Pronova BioPharma Norge AS).

EPA and DHA Products

In at least one embodiment, the fatty acid oil mixture comprises at least 75% EPA and DHA by weight of the fatty acid oil mixture, of which at least 95% is EPA. In another embodiment, the fatty acid oil mixture comprises at least 80% EPA and DHA by weight of the fatty acid oil mixture, of which at least 95% is EPA. In yet another embodiment, the fatty acid oil mixture comprises at least 90% EPA and DHA by weight of the fatty acid oil mixture, of which at least 95% is EPA.

In another embodiment, the fatty acid oil mixture comprises at least 75% EPA and DHA by weight of the fatty acid oil mixture, of which at least 95% is DHA. For example, in one embodiment, the fatty acid oil mixture comprises at least 80% EPA and DHA by weight of the fatty acid oil mixture, of which at least 95% is DHA. In another embodiment, the fatty acid oil mixture comprises at least 90% EPA and DHA by weight of the fatty acid oil mixture, of which at least 95% is DHA.

Supplement

The present disclosure further provides a food supplement or a nutritional supplement comprising a fatty acid oil mixture and at least one surfactant, wherein the fatty acid oil mixture comprises less than 75% EPA and DHA by weight of the fatty acid oil mixture. In some embodiments, for example, the fatty acid oil comprises less than 70% EPA and DHA by weight of the fatty acid oil mixture, such as less than 65%, less than 60%, less than 55%, less than 50%, less than 45%, less than 40%, or even less than 35% by weight of the fatty acid oil mixture.

In some embodiments, the fatty acid oil mixture comprises from about 25% to about 75% EPA and DHA by weight of the fatty acid oil mixture, such as from about 30% to about 75%, from about 30% to about 70%, from about 30% to about 65%, from about 30% to about 55%, from about 30% to about 50%, from about 30% to about 45%, from about 30% to about 40%, and further for example, from about 30% to about 35% EPA and DHA, by weight of the fatty acid oil mixture.

In some embodiments of the present disclosure, the fatty acids, such as omega-3 fatty acids, of the fatty acid oil mixture are esterified, such as alkyl esters. The alkyl esters may include, but are not limited to, ethyl, methyl, propyl, and butyl esters, and mixtures thereof. In other embodiments, the fatty acids are chosen from mono-, di-, and triglycerides. For example, the fatty acid oil mixture comprises from about 25% to about 75% EPA and DHA by weight of the fatty acid oil mixture in a form chosen from methyl ester, ethyl ester, and triglyceride.

Surfactant/Preconcentrate

The present disclosure further provides for a preconcentrate composition. As used herein, the term "preconcentrate" refers to a composition comprising a fatty acid oil mixture and at least one surfactant.

A surfactant may, for example, lower the surface tension of a liquid or the surface tension between two liquids. For example, surfactants according to the present disclosure may lower the surface tension between the fatty acid oil mixture and an aqueous solution.

Chemically speaking, surfactants are molecules with at least one hydrophilic part and at least one hydrophobic (i.e., lipophilic) part. Surfactant properties may be reflected in the hydrophilic-lipophilic balance (HLB) value of the surfactant, wherein the HLB value is a measure of the degree of hydrophilic versus lipophilic properties of a surfactant. The HLB value normally ranges from 0 to 20, where a HLB value of 0 represents high hydrophilic character, and a HLB of 20 represents high lipophilic character. Surfactants are often used in combination with other surfactants, wherein the HLB values are additive. The HLB value of surfactant mixtures may be calculated as follows:

$$HLB_A(\text{fraction of surfactant } A) + HLB_B(\text{fraction of surfactant } B) = HLB_{A+B \text{ mixture}}$$

Surfactants are generally classified as ionic surfactants, e.g., anionic or cationic surfactants, and nonionic surfactants. If the surfactant contains two oppositely charged groups, the surfactant is named a zwitterionic surfactant. Other types of surfactants include, for example, phospholipids.

In at least one embodiment of the present disclosure, the preconcentrate comprises at least one surfactant chosen from nonionic, anionic, cationic, and zwitterionic surfactants.

Non-limiting examples of nonionic surfactants suitable for the present disclosure are mentioned below.

Pluronic® surfactants are nonionic copolymers composed of a central hydrophobic polymer (polyoxypropylene(poly (propylene oxide))) with a hydrophilic polymer (polyoxyethylene(poly(ethylene oxide))) on each side. Various commercially-available Pluronic® products are listed in Table 1.

TABLE 1

Examples of Pluronic ® surfactants.

| | Type | Average Molecular Weight (D) | HLB Value |
|---|---|---|---|
| Pluronic ® L-31 | Non-ionic | 1100 | 1.0-7.0 |
| Pluronic ® L-35 | Non-ionic | 1900 | 18.0-23.0 |
| Pluronic ® L-61 | Non-ionic | 2000 | 1.0-7.0 |
| Pluronic ® L-81 | Non-ionic | 2800 | 1.0-7.0 |
| Pluronic ® L-64 | Non-ionic | 2900 | 12.0-18.0 |
| Pluronic ® L-121 | Non-ionic | 4400 | 1.0-7.0 |
| Pluronic ® P-123 | Non-ionic | 5800 | 7-9 |
| Pluronic ® F-68 | Non-ionic | 8400 | >24 |
| Pluronic ® F-108 | Non-ionic | 14600 | >24 |

Brij® are nonionic surfactants comprising polyethylene ethers. Various commercially-available Brij® products are listed in Table 2.

TABLE 2

Examples of Brij ® surfactants.

| | Type | Compound | HLB Value |
|---|---|---|---|
| Brij ® 30 | Non-ionic | Polyoxyethylene(4) lauryl ether | 9.7 |
| Brij ® 35 | Non-ionic | polyoxyethylene (23) lauryl ether | 16.9 |
| Brij ® 52 | Non-ionic | Polyoxyethylene (2) cetyl ether | 5.3 |
| Brij ® 56 | Non-ionic | Polyoxyethylene (10) cetyl ether | 12.9 |
| Brij ® 58 | Non-ionic | Polyoxyethylene (20) cetyl ether | 15.7 |
| Brij ® 72 | Non-ionic | polyoxyethylene (2) stearyl ether | 4.9 |
| Brij ® 76 | Non-ionic | polyoxyethylene (10) stearyl ether | 12.4 |
| Brij ® 78 | Non-ionic | polyoxyethylene (20) stearyl ether | 15.3 |
| Brij ® 92V | Non-ionic | Polyoxyethylene (2) oleyl ether | 4.9 |
| Brij ® 93 | Non-ionic | Polyoxyethylene (2) oleyl ether | 4 |
| Brij ® 96V | Non-ionic | polyethylene glycol oleyl ether | 12.4 |
| Brij ® 97 | Non-ionic | Polyoxyethylene (10) oleyl ether | 12 |
| Brij ® 98 | Non-ionic | Polyoxyethylene (20) oleyl ether | 15.3 |
| Brij ® 700 | Non-ionic | polyoxyethylene (100) stearyl ether | 18 |

Span® are nonionic surfactants comprising sorbitan esters. Span® is available from different sources including Aldrich. Various commercially-available Span® products are listed in Table 3.

TABLE 3

Examples of Span ® surfactants.

| | Type | Compound | HLB Value |
|---|---|---|---|
| Span ® 20 | Non-ionic | sorbitan monolaurate | 8.6 |
| Span ® 40 | Non-ionic | sorbitan monopalmitate | 6.7 |
| Span ® 60 | Non-ionic | sorbitan monostearate | 4.7 |
| Span ® 65 | Non-ionic | sorbitan tristearate | 2.1 |
| Span ® 80 | Non-ionic | sorbitan monooleate | 4.3 |
| Span ® 85 | Non-ionic | Sorbitan trioleate | 1.8 |

Tween® (polysorbates) are nonionic surfactants comprising polyoxyethylene sorbitan esters. Various commercially-available Tween® products are listed in Table 4.

TABLE 4

Examples of Tween ® surfactants.

| | Type | Compound | HLB Value |
|---|---|---|---|
| Tween ® 20 | Non-ionic | polyoxyethylene (20) sorbitan monolaurate | 16.0 |
| Tween ® 40 | Non-ionic | polyoxyethylene (20) sorbitan monopalmitate | 15.6 |
| Tween ® 60 | Non-ionic | polyoxyethylene sorbitan monostearate | 14.9 |
| Tween ® 65 | Non-ionic | polyoxyethylene sorbitan tristearate | 10.5 |
| Tween ® 80 | Non-ionic | polyoxyethylene(20) sorbitan monooleate | 15.0 |
| Tween ® 85 | Non-ionic | polyoxyethylene sorbane trioleate | 11.0 |

Myrj® are nonionic surfactants comprising polyoxyethylene fatty acid esters. Various commercially-available Myrj® products are listed in Table 5.

TABLE 5

Examples of Myrj ® surfactants.

| | Type | Compound | HLB Value |
|---|---|---|---|
| Myrj ® 45 | Non-ionic | polyoxyethylene monostearate | 11.1 |
| Myrj ® 49 | Non-ionic | polyoxyethylene monostearate | 15.0 |
| Myrj ® 52 | Non-ionic | polyoxyethylene monostearate | 16.9 |
| Myrj ® 53 | Non-ionic | polyoxyethylene monostearate | 17.9 |

Cremophor® are nonionic surfactants. Various commercially-available Cremophor® products are listed in Table 6.

TABLE 6

Examples of Cremophor ® surfactants.

| | Type | Compound | HLB Value |
|---|---|---|---|
| Cremophor ® REL | Non-ionic | polyoxyethylated castor oil | 2-14 |
| Cremophor ® RH40 | Non-ionic | hydrogenated polyoxyethylated castor oil | 14-16 |
| Cremophor ® RH60 | Non-ionic | hydrogenated polyoxyethylated castor oil | 15-17 |
| Cremophor ® RO | Non-ionic | hydrogenated polyoxyethylated castor oil | 16.1 |

According to the present disclosure, other exemplary nonionic surfactants include, but are not limited to, diacetyl monoglycerides, diethylene glycol monopalmitostearate, ethylene glycol monopalmitostearate, glyceryl behenate, glyceryl distearate, glyceryl monolinoleate, glyceryl monooleate, glyceryl monostearate, macrogol cetostearyl ether such as cetomacrogol 1000 and polyoxy 20 cetostearyl ether, macrogol 15 hydroxystearate, macrogol lauri ethers such as laureth 4 and lauromacrogol 400, macrogol monomethyl ethers, macrogol oleyl ethers such as polyoxyl 10 oleyl ether, macrogol stearates such as polyoxyl 40 stearate, menfegol, mono and diglycerides, nonoxinols such as nonoxinol-9, nonoxinol-10 and nonoxinol-11, octinols such as octoxinol 9 and oxtoxinol 10, polyoxamers such as polyoxalene, polyoxamer 188, polyoxamer 407, polyoxyl castor oil such as polyoxyl 35 castor oil, polyoxyl hydrogenated castor oil such as polyoxyl 40 hydrogenated castor oil, propylene glycol diacetate, propylene glycol laurates such as propylene glycol dilaurate and propylene glycol monolaurate. Further examples include propylene glycol monopalmitostearate, quillaia, sorbitan esters, and sucrose esters.

Anionic surfactants suitable for the present disclosure include, for example, salts of perfluorocarboxylic acids and perfluorosulphonic acid, alkyl sulphate salts such as sodium dodecyl sulphate and ammonium lauryl sulphate, sulphate ethers such as sodium lauryl ether sulphate, and alkyl benzene sulphonate salts.

Cationic surfactants suitable for the present disclosure include, for example, quaternary ammonium compounds such as benzalkonium chloride, cetylpyridinium chlorides, benzethonium chlorides, and cetyl trimethylammonium bromides or other trimethylalkylammonium salts.

Zwitterionic surfactants include, but are limited to, for example dodecyl betaines, coco amphoglycinates and cocamidopropyl betaines.

In some embodiments of the present disclosure, the surfactant may comprise a phospholipid, derivative thereof, or analogue thereof. Such surfactants may, for example, be chosen from natural, synthetic, and semisynthetic phospholipids, derivatives thereof, and analogues thereof. Phospholipids may be "natural" or from a marine origin chosen from, e.g., phosphatidylcholine, phosphatidylethanolamine, phosphatidylserine, and phosphatidylinosytol. The fatty acid moiety may be chosen from 14:0, 16:0, 16: 1n-7, 18:0, 18:1n-9, 18:1n-7, 18:2n-6, 18:3n-3, 18:4n-3, 20:4n-6, 20:5n-3, 22:5n-3 and 22:6n-3, or any combinations thereof. In one embodiment, the fatty acid moiety is chosen from palmitic acid, EPA and DHA. Exemplary phospholipids surfactants include phosphatidylcholines with saturated, unsaturated and/or polyunsaturated lipids such as dioleoylphosphatidylcholine, dipentadecanoylphosphatidylcholine, dilauroylphosphatidylcholine, dimyristoylphosphatidylcholine, dipalmitoylphosphatidylcholine, distearoylphosphatidylcholine, dieicopentaenoyl(EPA)choline, didocosahexaenoyl(DHA)choline, phosphatidylethanolamines, phosphatidylglycerols, phosphatidylserines and phosphatidylinositols. Other exemplary phospholipid surfactants include soybean lecithin, egg lecithin, diolelyl phosphatidylcholine, distearoyl phosphatidyl glycerol, PEG-ylated phospholipids, and dimyristoyl phosphatidylcholine.

Other exemplary surfactants suitable for the present disclosure are listed in Table 7.

TABLE 7

Other surfactants

| Surfactant | Type | HBL Value |
| --- | --- | --- |
| Ethylene glycol distearate | Nonionic | 1.5 |
| Glyceryl monostearate | Nonionic | 3.3 |
| Propylene glycol monostearate | Nonionic | 3.4 |
| Glyceryl monostearate | Nonionic | 3.8 |
| Diethylene glycol monolaurate | Nonionic | 6.1 |
| Acacia | Anionic | 8.0 |
| Cetrimonium bromide | Cationic | 23.3 |
| Cetylpyridinium chloride | Cationic | 26.0 |
| Polyoxamer 188 | Nonionic | 29.0 |
| Sodium lauryl sulphate | Anionic | 40 |

In some embodiments of the present disclosure, the at least one surfactant does not comprise Labrasol, Cremophor RH40, or the combination of Cremophor and Tween-80.

In some embodiments, the at least one surfactant has a hydrophilic-lipophilic balance (HLB) of less than about 10, such as less than about 9, or less than about 8.

Co-Surfactant

In some embodiments, compositions of the present disclosure further comprise at least one co-surfactant. As used herein the term "co-surfactant" means a substance added to the preconcentrate in combination with the at least one surfactant to affect, e.g., increase or enhance, emulsification and/or stability of the preconcentrate, for example to aid in forming an emulsion. In some embodiments, the at least one co-surfactant is hydrophilic. In some embodiments, the at least one co-surfactant is not in free acid form.

Examples of co-surfactants suitable for the present disclosure include, but are not limited to, short chain alcohols comprising from 1 to 6 carbons (e.g., ethanol), benzyl alcohol, alkane diols and triols (e.g., propylene glycol, glycerol, polyethylene glycols such as PEG and PEG 400), glycol ethers such as tetraglycol and glycofurol (e.g., tetrahydrofurfuryl PEG ether), pyrrolidine derivatives such as N-methylpyrrolidone (e.g., Pharmasolve®) and 2-pyrrolidone (e.g., Soluphor® P), and bile salts, for example sodium deoxycholate. Further examples include ethyl oleate.

In some embodiments, the at least one co-surfactant comprises from about 1% to about 10%, by weight relative to the weight of the preconcentrate.

Solvent

In some embodiments, compositions according to the present disclosure, such as the preconcentrate, further comprises at least one solvent. As used herein, the term "solvent" means a substance added to the preconcentrate to affect and/or alter the consistency of the preconcentrate, for example in an aqueous solution. In some embodiments, the solvent is hydrophilic. Hydrophilic solvents suitable for the present disclosure include, but are not limited to, alcohols, including water-miscible alcohols, such as absolute ethanol and/or glycerol, and glycols, for example glycols obtainable from an oxide such as ethylene oxide, such as 1,2-propylene glycol. Other non-limiting examples include polyols, such as polyalkylene glycol, e.g., poly($C_{2-3}$)alkylene glycol such as polyethylene glycol. In at least one embodiment, the at least one solvent is a pharmaceutically-acceptable solvent.

In some embodiments of the present disclosure, the preconcentrate comprises at least one substance that acts both as a co-surfactant and a solvent, for example an alcohol such as ethanol. In other embodiments, the preconcentrate comprises at least one co-surfactant and at least one solvent that are different substances. For example, in some embodiments the preconcentrate comprises ethanol as the co-surfactant and glycerol as the solvent.

In some embodiments of the present disclosure, the preconcentrate is a pharmaceutical preconcentrate comprising a fatty acid oil mixture comprising at least 75% eicosapentaenoic acid (EPA) and docosahexaenoic acid (DHA), by weight of the fatty acid oil mixture, wherein the EPA and DHA are in a form chosen from ethyl ester and triglyceride; and at least one surfactant.

In one embodiment, the pharmaceutical preconcentrate comprises: a fatty acid oil mixture comprising at least 95% of EPA ethyl ester, DHA ethyl ester, or mixtures thereof, by weight of the fatty acid oil mixture; and a least one surfactant chosen from polysorbate 20, polysorbate 80, and mixtures thereof.

In another embodiment, the pharmaceutical preconcentrate comprises: a fatty acid oil mixture comprising from about 80% to about 88% EPA and DHA by weight of the fatty acid oil mixture, wherein the EPA and DHA are in ethyl ester form; and at least one surfactant chosen from polysorbate 20, polysorbate 80, and mixtures thereof; wherein the at least one surfactant comprises less than 40%, by weight relative to the weight of the preconcentrate.

In another embodiment, the pharmaceutical preconcentrate comprises: a fatty acid oil mixture comprising from about 80% to about 88% EPA and DHA by weight of the fatty acid oil mixture, wherein the EPA and DHA are in ethyl ester form; and at least one surfactant chosen from polysorbate 20, polysorbate 80, and mixtures thereof; wherein the at least one surfactant comprises less than 35%, by weight relative the weight of the preconcentrate.

In some embodiments, for example, the pharmaceutical preconcentrate comprises K85EE as the fatty acid oil mixture, and at least one surfactant chosen from polysorbate 20, polysorbate 80, and mixtures thereof.

In another embodiment, the pharmaceutical preconcentrate comprises a fatty acid oil mixture comprising from about 80% to about 88% EPA and DHA, by weight of the fatty acid oil mixture, wherein the EPA and DHA are in ethyl ester form; at least one surfactant chosen from polysorbate 80; and at least one co-surfactant comprising ethanol.

In some embodiments, the pre-concentrate is in the form of a gelatin capsule or loaded into a tablet.

In other embodiments, the preconcentrate is a food supplement preconcentrate or nutritional supplement preconcentrate comprising a fatty acid oil mixture comprising from about 25% to about 75% EPA and DHA, by weight of the fatty acid oil mixture, wherein the EPA and DHA are in a form chosen from ethyl ester and triglyceride; and at least one surfactant.

In some embodiments, the weight ratio of fatty acid oil mixture:total surfactant of the preconcentrate ranges from about 1:1 to about 200:1, from about 1:1 to about 100:1, from about 1:1 to about 50:1, from about 1:1 to about 10:1, from about 1:1 to about 8:1, from about 1.1 to 6:1 from about 1:1 to about 5:1, from about 1:1 to about 4:1, or from about 1:1 to about 3:1.

In some embodiments, the at least one surfactant comprises from about 0.5% to about 40%, by weight relative to the total weight of the preconcentrate. For example, in some embodiments, the at least one surfactant comprises from about 1% to about 35%, from about 5% to about 35%, from about 10% to about 35%, from about 15% to about 35%, from about 15% to about 30%, or from about 20% to about 30%, by weight, relative to the total weight of the preconcentrate. In one embodiment, the at least one surfactant comprises about 20%, by weight relative to the total weight of the preconcentrate.

SNEDDS/SMEDDS/SEDDS

The preconcentrate of the present disclosure may be in a form of a self-nanoemulsifying drug delivery system (SNEDDS), a self-microemulsifying drug delivery system (SMEDDS), or a self emulsifying drug delivery system (SEDDS), wherein the preconcentrate forms an emulsion in an aqueous solution.

Without being bound by theory, it is believed that the preconcentrate forms a SNEDDS, SMEDDS, and/or SEDDS upon contact with gastric and/or intestinal media in the body, wherein the preconcentrate forms an emulsion comprising micelle particles. The emulsion may, for example, provide for increased or improved stability of the fatty acids for uptake in the body and/or provide increased surface area for absorption. SNEDDS/SMEDDS/SEDDS may thus provide for enhanced or improved hydrolysis, solubility, bioavailability, absorption, or any combinations thereof of fatty acids in vivo.

Generally, known SNEDDS/SMEDDS/SEDDS formulations comprise ~10 mg of a drug and ~500 mg of surfactants/co-surfactants. The SNEDDS/SMEDDS/SEDDS presently disclosed may have the opposite relationship, i.e., the amount of fatty acid oil mixture comprising the active pharmaceutical ingredient (API) is greater than the amount of surfactant.

The SNEDDS/SMEDDS/SEDDS presently disclosed may comprise a particle size (i.e., particle diameter) ranging from about 5 nm to about 10 μm. For example, in some embodiments, the particle size ranges from about 5 nm to about 1 μm, such as from about 50 nm to about 750 nm, from about 100 nm to about 500 nm, or from about 150 nm to about 350 nm.

Excipients

The compositions presently disclosed may further comprise at least one non-active pharmaceutical ingredient, e.g., excipient. Non-active ingredients may solubilize, suspend, thicken, dilute, emulsify, stabilize, preserve, protect, color, flavor, and/or fashion active ingredients into an applicable and efficacious preparation, such that it may be safe, convenient, and/or otherwise acceptable for use. The at least one non-active ingredient may be chosen from colloidal silicon dioxide, crospovidone, lactose monohydrate, lecithin, microcrystalline cellulose, polyvinyl alcohol, povidone, sodium lauryl sulfate, sodium stearyl fumarate, talc, titanium dioxide, and xanthum gum.

The compositions presently disclosed may further comprise at least one antioxidant. Examples of antioxidants suitable for the present disclosure include, but are not limited to, α-tocopherol (vitamin E), calcium disodium EDTA, alpha tocoferyl acetates, butylhydroxytoluenes (BHT), and butylhydroxyanisoles (BHA).

The compositions presently disclosed may further comprise at least one superdistintegrant. Superdisintegrants may, for example, improve disintegrant efficiency resulting in decreased use levels in comparison to traditional disintegrants. Examples of superdisintegrants include, but are not limited to, crosscarmelose (a crosslinked cellulose), crospovidone (a crosslinked polymer), sodium starch glycolate (a crosslinked starch), and soy polysaccharides. Commercial examples of superdisintegrants include Kollidon® (BASF), Polyplasdone® XL (ISP), and Ac-Di-Sol (FMC BioPolymer).

In some embodiments of the present disclosure, the composition comprises from about 1% to about 25% of at least one superdisintegrant by weight of the composition, such as from about 1% to about 20% by weight, or from about 1% to about 15% by weight of the composition. In some embodiments, the compositions comprising at least one superdisintegrant are in a tablet form.

The compositions presently disclosed may be administered, e.g., in capsule, tablet or any other drug delivery forms. For example, the composition may be encapsulated, such as in a gelatin capsule. In some embodiments, the preconcentrate is encapsulated in a gelatin capsule.

In some embodiments of the present disclosure, the capsule fill content ranges from about 0.400 g to about 1.600 g. For example, in some embodiments, the capsule fill content ranges from about 0.400 g to about 1.300 g, from about 0.600 g to about 1.200 g, from about 0.600 g to about 0.800 g, from about 0.800 g to about 1.000, from about 1.000 g to about 1.200 g, or any amount in between. For example, in some embodiments the capsule fill content is about 0.600 g, about 0.800 g, about 1.000 g, or about 1.200 g.

The capsules presently disclosed may be manufactured in low oxygen conditions to inhibit oxidation during the manufacturing process. Preparation of capsules and/or microcapsules in accordance with the present disclosure may be carried out following any of the methods described in the literature. Examples of such methods include, but are not limited to, simple coacervation methods (see, e.g., ES 2009346, EP 0052510, and EP 0346879), complex coacervation methods (see, e.g., GB 1393805), double emulsion methods (see, e.g., U.S. Pat. No. 4,652,441), simple emulsion methods (see, e.g., U.S. Pat. No. 5,445,832), and solvent evaporation methods (see, e.g., GB 2209937). Those methods may, for example, provide for continuous processing and flexibility of batch size.

Methods or Uses

The present disclosure further encompasses methods of treating and/or regulating at least one health problem in a subject in need thereof. The compositions presently disclosed may be administered, e.g., in capsule, tablet or any other drug delivery forms, to a subject for therapeutic treatment and/or regulation of at least one health problem including, for example, irregular plasma lipid levels, cardiovascular functions, immune functions, visual functions, insulin action, neuronal development, heart failure, and post myocardial infarction. In some embodiments, the at least one health problem is chosen from mixed dyslipidemia, dyslipidemia, hypertriglyceridemia, hypercholesterolemia, heart failure, and post-myocardial infarction.

In one embodiment, there is a method of treating at least one health problem in a subject in need thereof, comprising administering to the subject a pharmaceutical preconcentrate comprising a pharmaceutically-effective amount of a fatty acid oil mixture comprising at least 75% eicosapentaenoic acid (EPA) and docosahexaenoic acid (DHA), by weight of the fatty acid oil mixture, wherein the EPA and DHA are in a form chosen from ethyl ester and triglyceride; and at least one surfactant. In some embodiments, the method treats at least one of elevated triglyceride levels, non-HDL cholesterol levels, LDL cholesterol levels and/or VLDL cholesterol levels.

In another embodiment, there is a method of regulating at least one health problem in a subject in need thereof, comprising administering to the subject administering to the subject a supplement preconcentrate comprising: a fatty acid oil mixture comprising from about 25% to about 75% eicosapentaenoic acid (EPA) and docosahexaenoic acid (DHA), by weight of the fatty acid oil mixture, wherein the EPA and DHA are in a form chosen from ethyl ester and triglyceride; and at least one surfactant; wherein the at least one health problem is chosen from irregular plasma lipid levels, cardiovascular functions, immune functions, visual functions, insulin action, neuronal development, heart failure, and post myocardial infarction.

In some embodiments, the pharmaceutical or supplement preconcentrate forms a self-nanoemulsifying drug delivery system (SNEDDS), a self-microemulsifying drug delivery system (SMEDDS), or a self-emulsifying drug delivery system (SEDDS) in an aqueous solution. In some embodiments, the aqueous solution is gastric media and/or intestinal media.

The total daily dosage of the fatty acid oil mixture may range from about 0.600 g to about 6.000 g. For example, in some embodiments, the total dosage of the fatty acid oil mixture ranges from about 0.800 g to about 4.000 g, from about 1.000 g to about 4.000 g, or from about 1.000 g to about 2.000 g. In one embodiment, the fatty acid oil mixture is chosen from K85EE and AGP 103 fatty acid oil compositions.

The preconcentrates presently disclosed may be administered in from 1 to 10 dosages, such as from 1 to 4 times a day, such as once, twice, three times, or four times per day, and further for example, once, twice or three times per day. The administration may be oral or any other form of administration that provides a dosage of fatty acids, e.g., omega-3 fatty acids, to a subject.

The following examples are intended to illustrate the present disclosure without, however, being limiting in nature. It is understood that the skilled artisan will envision additional embodiments consistent with the disclosure provided herein.

EXAMPLES

Example 1

Compatibility of Preconcentrates with Solvents

The compatibility of solvents and a preconcentrate having a fixed amount of K85EE and Tween-80 were evaluated. The preconcentrates described in Table 8 were prepared according to the schemes below on a weight to weight basis. The preconcentrates were visually inspected after mixing and again after being stored for 24 hours at room temperature. Under the Preconcentrate heading, a "clear" designation represents a transparent homogenous mixture; a "turbid" designation represents a nonhomogenous mixture, where some turbidity can be observed by visual inspection. The degree of turbidity was not determined.

TABLE 8

Compatibility of Solvent and Preconcentrates.

| K85-EE (mg) | Tween-80 (mg) | 96% ethanol (mg) | 96% ethanol (%) | Preconcentrate |
|---|---|---|---|---|
| 400 | 110 | 10.7 | 2.1 | Turbid |
| 400 | 110 | 18.7 | 3.5 | Turbid |
| 400 | 110 | 28.4 | 5.3 | Turbid |
| 400 | 110 | 32.1 | 5.9 | Turbid |
| 400 | 110 | 45.7 | 8.2 | Turbid |
| 400 | 110 | 53.5 | 9.5 | Turbid |
| 400 | 110 | 61.5 | 10.8 | Turbid |
| 400 | 110 | 69.8 | 12.0 | Turbid |
| 400 | 110 | 79.9 | 13.5 | Turbid |
| 400 | 110 | 91.3 | 15.2 | Turbid |
| 400 | 110 | 102.5 | 16.7 | Turbid |

| K85-EE (mg) | Tween-80 (mg) | Propylene glycol (mg) | Propylene glycol (%) | Preconcentrate |
|---|---|---|---|---|
| 400 | 110 | 11.1 | 2.1 | Turbid |
| 400 | 110 | 16.7 | 3.2 | Turbid |
| 400 | 110 | 23.1 | 4.3 | Turbid |
| 400 | 110 | 32.9 | 6.1 | Turbid |
| 400 | 110 | 41.5 | 7.5 | Turbid |
| 400 | 110 | 48.6 | 8.7 | Turbid |
| 400 | 110 | 59.9 | 10.5 | Turbid |
| 400 | 110 | 72.9 | 12.5 | Turbid |
| 400 | 110 | 81.5 | 13.8 | Turbid |
| 400 | 110 | 93.5 | 15.5 | Turbid |
| 400 | 110 | 104.6 | 17.0 | Turbid |

| K85-EE (mg) | Tween-80 (mg) | PEG 300 (mg) | PEG 300 (%) | Preconcentrate |
|---|---|---|---|---|
| 400 | 110 | 13.9 | 2.7 | Turbid |
| 400 | 110 | 23.7 | 4.4 | Turbid |
| 400 | 110 | 35.6 | 6.5 | Turbid |
| 400 | 110 | 47.1 | 8.5 | Turbid |
| 400 | 110 | 55.0 | 9.7 | Turbid |
| 400 | 110 | 68.7 | 11.9 | Turbid |
| 400 | 110 | 81.8 | 13.8 | Turbid |
| 400 | 110 | 90.3 | 15.0 | Turbid |
| 400 | 110 | 104.0 | 16.9 | Turbid |

TABLE 8-continued

Compatibility of Solvent and Preconcentrates.

| K85-EE (mg) | Tween-80 (mg) | Benzyl alcohol (mg) | Benzyl alcohol (%) | Preconcentrate |
|---|---|---|---|---|
| 400 | 110 | 0 | 0 | Clear |
| 400 | 110 | 11.4 | 2.2 | Turbid |
| 400 | 110 | 18.1 | 3.4 | Turbid |
| 400 | 110 | 30.9 | 5.7 | Clear |
| 400 | 110 | 45.5 | 8.2 | Clear |
| 400 | 110 | 55.6 | 9.8 | Clear |
| 400 | 110 | 66.7 | 11.6 | Clear |
| 400 | 110 | 77.4 | 13.2 | Clear |
| 400 | 110 | 92.1 | 15.3 | Clear |
| 400 | 110 | 99.0 | 16.3 | Clear |

| K85-EE (mg) | Tween-80 (mg) | Triacetin (mg) | Triacetin (%) | Preconcentrate |
|---|---|---|---|---|
| 400 | 110 | 12.3 | 2.4 | Turbid |
| 400 | 110 | 24.3 | 4.5 | Turbid |
| 400 | 110 | 35.8 | 6.6 | Turbid |
| 400 | 110 | 45.3 | 8.2 | Turbid |
| 400 | 110 | 57.0 | 10.1 | Turbid |
| 400 | 110 | 68.1 | 11.8 | Turbid |
| 400 | 110 | 80.9 | 13.7 | Turbid |
| 400 | 110 | 90.0 | 15.0 | Turbid |
| 400 | 110 | 101.7 | 16.6 | Turbid |

| K85-EE (mg) | Tween-80 (mg) | 1-octa-decanol 99% (mg) | 1-octa-decanol 99% (%) | Preconcentrate |
|---|---|---|---|---|
| 400 | 110 | 8.6 | 1.7 | Precipitate |

| K85-EE (mg) | Tween-80 (mg) | oleyl alcohol 85% (mg) | oleyl alcohol 85% (%) | Preconcentrate |
|---|---|---|---|---|
| 400 | 100 | 13.0 | 2.5 | Turbid |
| 400 | 100 | 26.5 | 4.9 | Turbid |
| 400 | 100 | 37.3 | 6.8 | Turbid |
| 400 | 100 | 49.5 | 8.8 | Turbid |
| 400 | 100 | 62.6 | 10.9 | Turbid |
| 400 | 100 | 77.7 | 13.2 | Turbid |
| 400 | 100 | 92.2 | 15.3 | Turbid |
| 400 | 100 | 105.7 | 17.2 | Turbid |

| K85-EE (mg) | Tween-80 (mg) | 1-tetra-decanol 97% (mg) | 1 tetra-decanol 97% (%) | Preconcentrate |
|---|---|---|---|---|
| 400 | 100 | 1.7 | 0.3 | Turbid |
| 400 | 100 | 10.3 | 2.0 | Turbid |
| 400 | 100 | 22.7 | 4.3 | Turbid |
| 400 | 100 | 35.8 | 6.6 | Precipitate |

| K85-EE (mg) | Tween-80 (mg) | glycerol (mg) | glycerol (%) | Preconcentrate |
|---|---|---|---|---|
| 400 | 100 | 17.7 | 3.4 | Turbid |
| 400 | 100 | 28.0 | 5.2 | Turbid |
| 400 | 100 | 41.7 | 7.6 | Turbid |
| 400 | 100 | 52.8 | 9.4 | Turbid |
| 400 | 100 | 71.2 | 12.3 | Turbid |
| 400 | 100 | 85.4 | 14.3 | Turbid |
| 400 | 100 | 92.3 | 15.3 | Turbid |
| 400 | 100 | 105.7 | 17.2 | Turbid |

| K85-EE (mg) | Tween-80 (mg) | Oleic acid 90% (mg) | Oleic acid 90% (%) | Preconcentrate |
|---|---|---|---|---|
| 400 | 100 | 13.2 | 2.5 | Turbid |
| 400 | 100 | 23.9 | 4.5 | Turbid |
| 400 | 100 | 31.5 | 5.8 | Turbid |
| 400 | 100 | 41.4 | 7.5 | Turbid |
| 400 | 100 | 51.8 | 9.2 | Turbid |
| 400 | 100 | 65.2 | 11.3 | Clear |
| 400 | 100 | 79.8 | 13.5 | Clear |
| 400 | 100 | 87.2 | 14.6 | Clear |
| 400 | 100 | 102.2 | 16.7 | Clear |

| K85-EE (mg) | Tween-80 (mg) | 1-docosanol 98% (mg) | 1-docosanol 98% (%) | Preconcentrate |
|---|---|---|---|---|
| 400 | 100 | 9.6 | 1.8 | Precipitate |

Example 2

Lipolysis and Solubilization

Studies were done to analyze the rate of lipolysis (i.e., hydrolysis) and solubilization for different preconcentrates comprising K85EE and different free fatty acids and surfactants. Specifically, four experiments were designed to determine how the amount of surfactant influences the rate and extent of lipolysis and solubilization. The lipolysis was conducted on SMEDDS formulations comprising K85EE.

Materials

Bile salts: Porcine Bile extract (Sigma); contains glycine and taurine conjugates of hyodeoxycholic acid and other bile salts.

Pancreatic lipase, Porcine pancreas (Sigma); contains many enzymes, including amylase, trypsin, lipase, ribonuclease and protease.

Lechitin: Phospholipids (LIPOID S PC from LIPOID AG)

Trizma maleate (Sigma Aldrich)

Tween 20, Molecular Biology Grade (AppliChem Darmstadt), Tween 80 (Fluka)

α-Linoleic acid (Sigma 60%), Oleic acid (Aldrich 90%)

K85-EE and K85-FA

Preconcentrates A-E were prepared as summarized in Table 9.

TABLE 9

Preconcentrates A-E.

| Preconcentrate | Fatty acid oil mixture | Free fatty acid | Surfactant |
|---|---|---|---|
| A | K85EE (400 mg) | oleic acid (100 mg) | Tween 20 (300 mg) |
| B | K85EE (400 mg) | oleic acid (100 mg) | Tween 20 (75 mg) |
| C | K85EE (500 mg) | linoleic acid (100 mg) | Tween 80 (200 mg) |
| D | K85EE (400 mg) | K85FA (100 mg) | Tween 20 (300 mg) |
| E | K85EE (400 mg) | — | Tween 80 (100 mg) |

Lipolysis General Procedure

The in vitro dynamic lipolysis model developed by Zangenberg et al. (Zangenberg, N. H. et al., *Eur. J. Pharm. Sci.* 14, 237-244, 2001; Zangenberg, N. H., et al., *Eur. J. Pharm. Sci.* 14, 115-122, 2001) was used with slight modifications. The lipolysis was conducted in a thermostated 600 ml jacketed glass vessel in the presence of porcine bile extract, with continuous addition calcium chloride. The lipase source was porcine pancreatin and the hydrolysis was followed by titration with sodium hydroxide solution (1.0 N) using a pH stat (pH 6.5). The initial composition of the lipolysis media is shown in Table 10.

TABLE 10

Initial composition of lipolysis media.

| Substance | Initial concentration |
|---|---|
| Pancreatic lipase, Porcine pancreas | 800 USP units/ml |
| Bile salts, Porcine Bile extract | 5 mM |
| Phospholipids, LIPOID S PC from LIPOID AG | 1.25 mM |
| Trizma maleate | 2 mM |
| Na$^+$ | 150 mM |
| K85-EE | 5.58 mg/ml |

The final volume in all experiments was 300 ml and the calcium dispensing rate during the experiments was 0.045 mmol/min (0.09 ml/min). In all experiments, the amount of K85-EE added corresponds to 5.58 mg/ml.

To determine the course of K85-EE lipolysis by HPLC, crude samples were withdrawn and acidified with dilute hydrochloric acid. The concentrations of EPA-EE, DHA-EE, EPA-FA and DHA-FA were determined by HPLC in triplicate. Experiments were performed with LC Agilent Technologies 1200 series at a column temperature of 30° C., mobile phase (A) water (0.1% acetic acid) and (B) MeCN (0.1% acetic acid), with gradient: 0 to 8 minutes, from 70% B to 100% B; 8 to 15 minutes, 100% B; 16 to 16 minutes: from 100% B to 70% B, 16 to 20 minutes: 70% B. The flow rate was 0.5 ml/min, UV @ 210 nM, injection volume: 5 µl, and run time: 20 minutes.

Concentrations of EPA ethyl ester (EPA-EE), DHA ethyl ester (DHA-EE), EPA free acid (EPA-FA), and DHA free acid (DHA-FA) were monitored over time and the rate of lipolysis calculated as shown in Table 11 for comparison with Omacor®.

TABLE 11

Lipolysis of EPA and DHA ethyl ester in comparison to Omacor ®.

| | EPA-EE lipolysis (µg/ml/min) | DHA-EE lipolysis (µg/ml/min) | % lipolysis K85EE at t = 233 min |
|---|---|---|---|
| Omacor | 1.5 | 2.3 | 17 |
| A | 2.8 | 4.5 | 41 |
| B | 2.9 | 3.9 | 35 |
| C | 3.7 | 5.0 | 47 |
| D | 3.5 | 5.0 | 55 |
| E | 3.8 | 4.3 | 45 |

Figure 3:
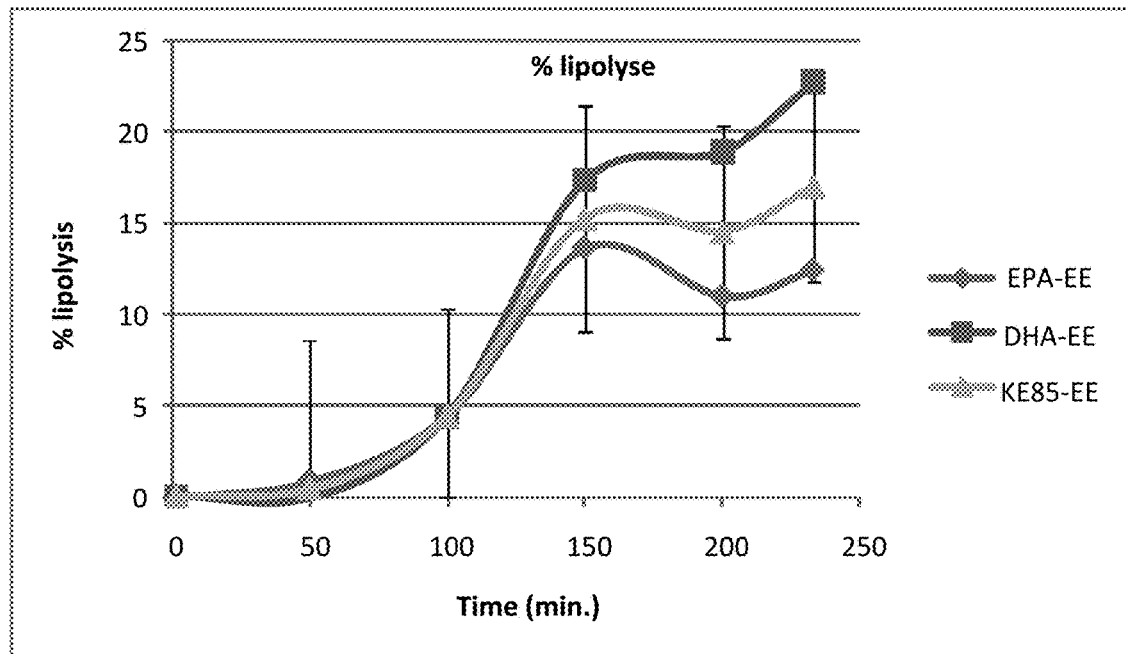
FIG. 3 shows the percent lipolysis of EPA-EE, DHA-EE and total K85EE at different time points for Omacor®.
Figure 4:
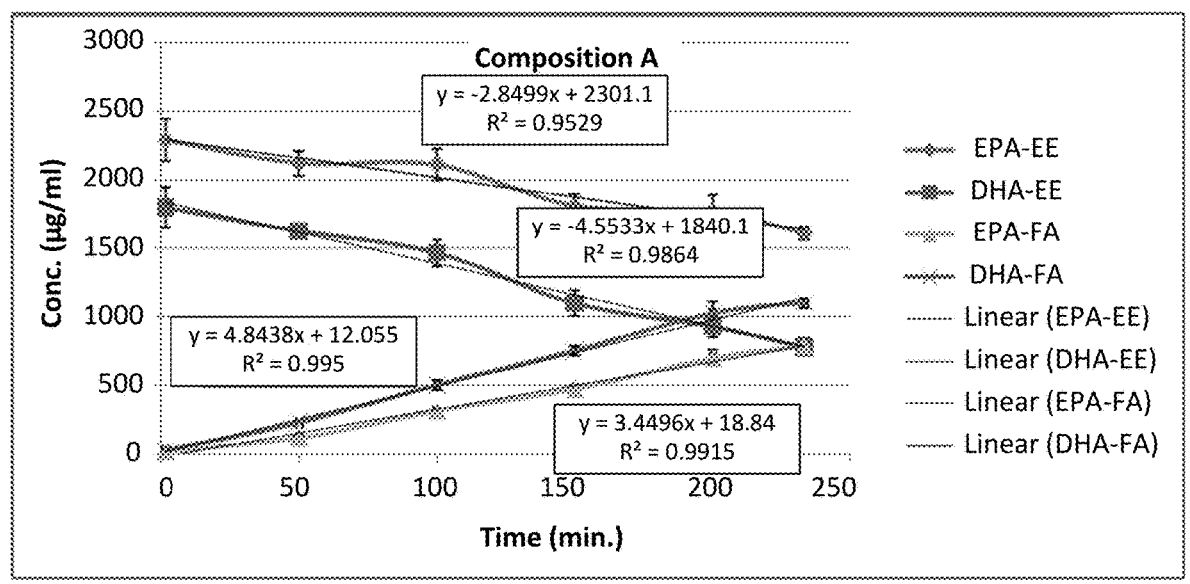
FIG. 4 shows the disappearance of EPA-EE and DHA-EE and the appearance of EPA-FA and DHA-FA during lipolysis of preconcentrate A.
Figure 7:
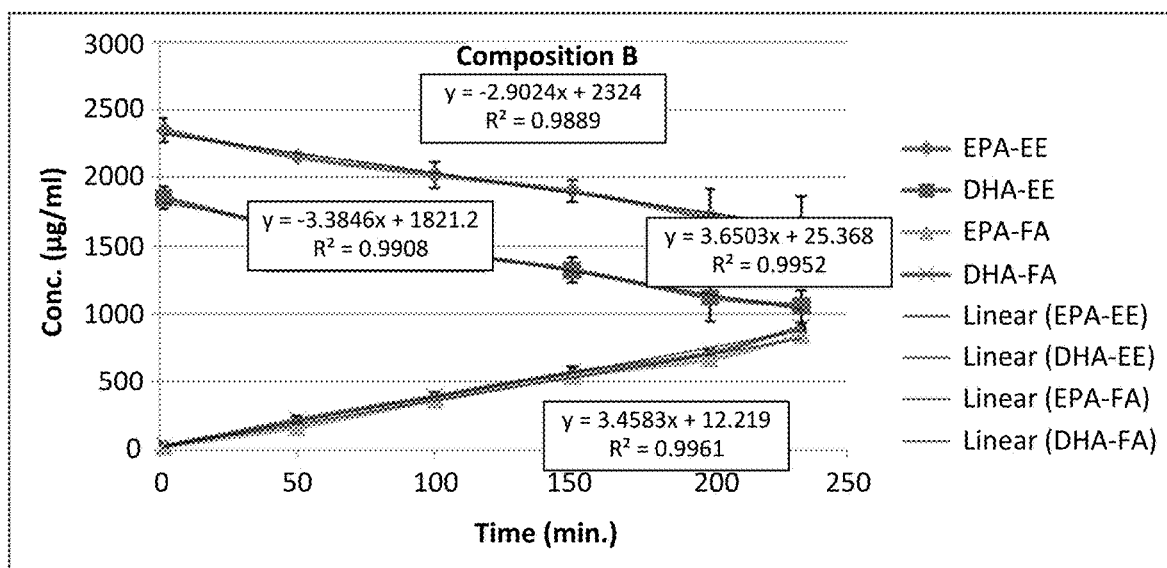
FIG. 7 shows the disappearance of EPA-EE and DHA-EE and the appearance of EPA-FA and DHA-FA during lipolysis of preconcentrate B.
Figure 10:
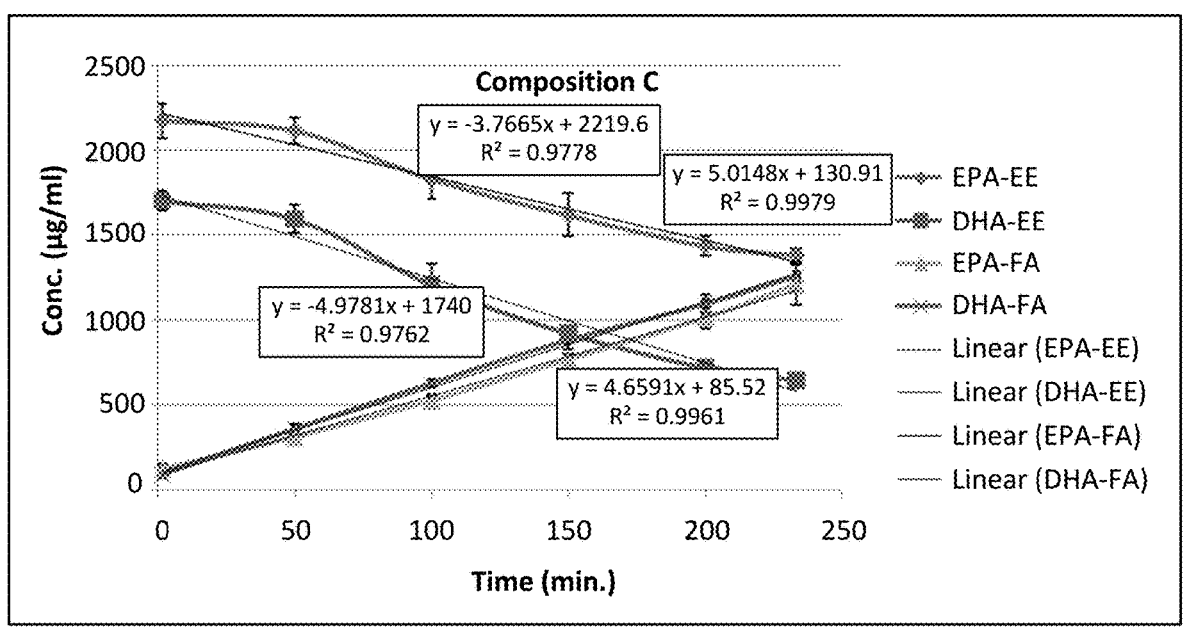
FIG. 10 shows the disappearance of EPA-EE and DHA-EE and the appearance of EPA-FA and DHA-FA during lipolysis of preconcentrate C.
Figure 16:
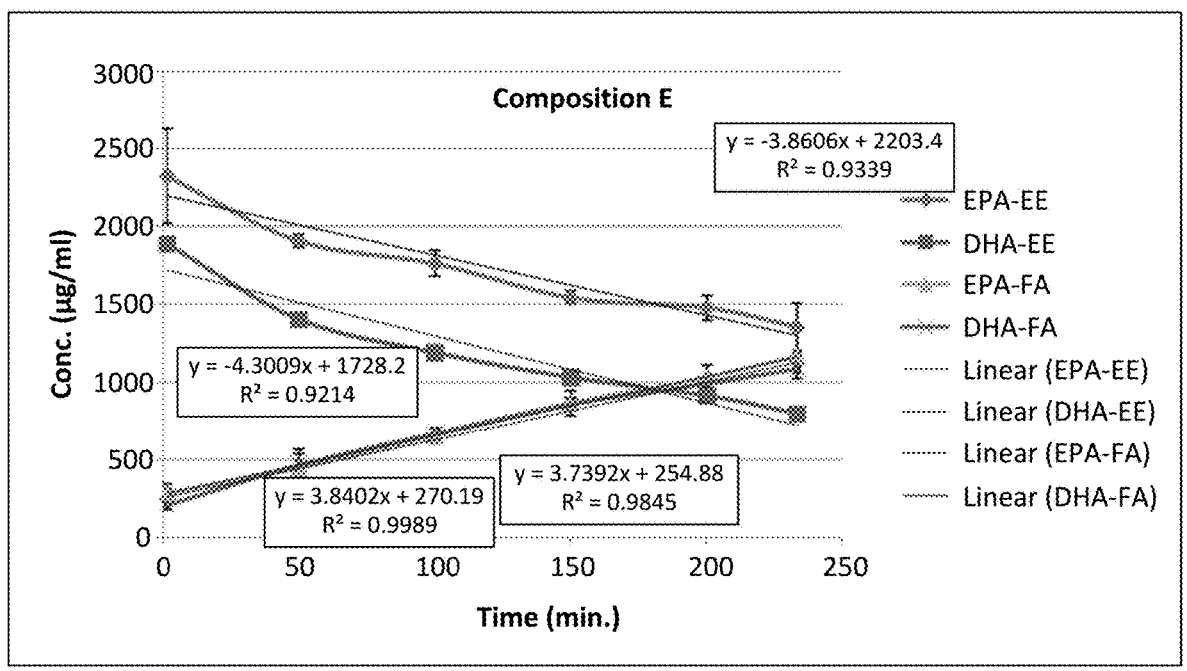
FIG. 16 shows the disappearance of EPA-EE and DHA-EE and the appearance of EPA-FA and DHA-FA during lipolysis of preconcentrate E.

FIGS. 1, 4, 7, 10, 3, and 16 graphically illustrate the disappearance of EPA-EE and DHA-EE and the appearance of EPA-FA and DHA-FA during lipolysis of each respective sample examined. Sample points from 2 minutes to 233 minutes were included in the graphs. In addition, linear regression lines have been included.

Figure 2:
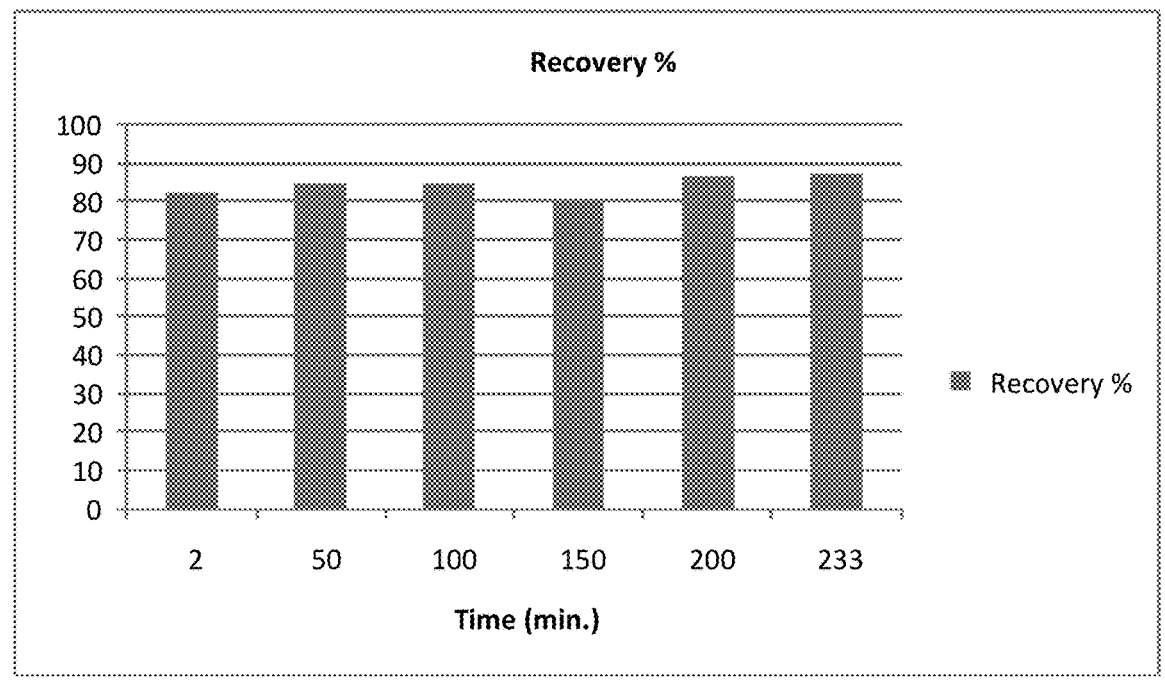
FIG. 2 shows the percent recovery of EPA+DHA at different time-points for Omacor®.
Figure 5:
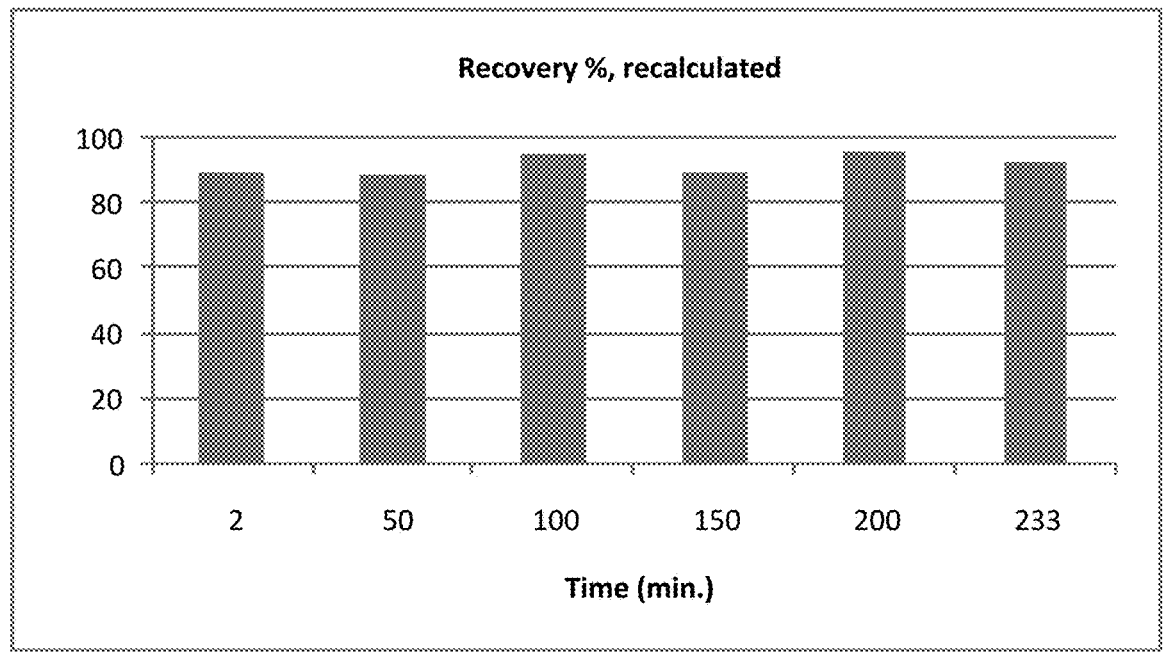
FIG. 5 shows the percent recovery of EPA+DHA at different time-points for preconcentrate A.
Figure 8:
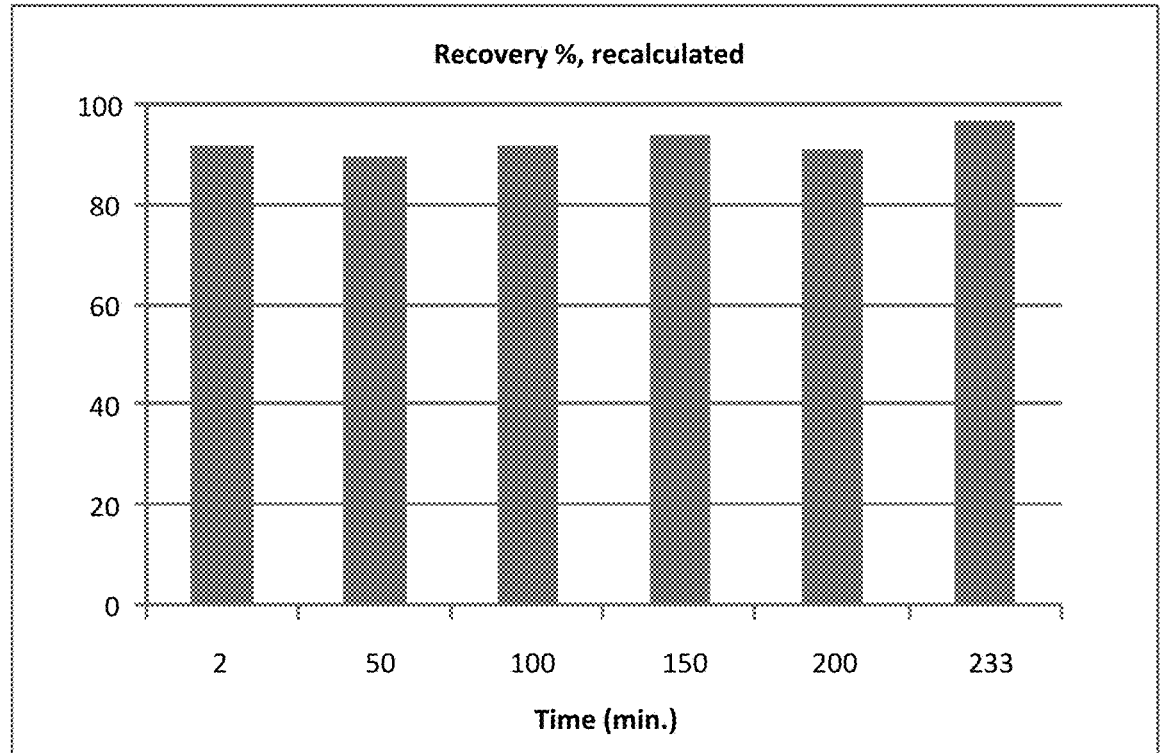
FIG. 8 shows the percent recovery of EPA+DHA at different time-points for preconcentrate B.
Figure 11:
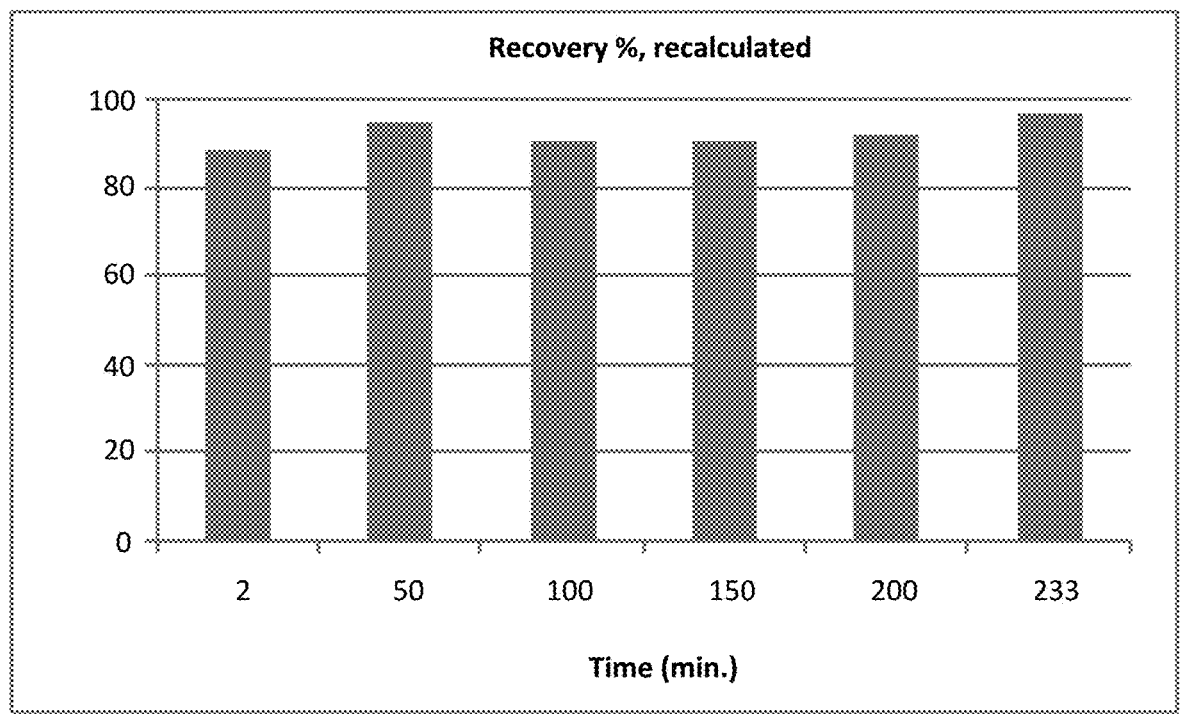
FIG. 11 shows the percent recovery of EPA+DHA at different time-points for preconcentrate C.
Figure 14:
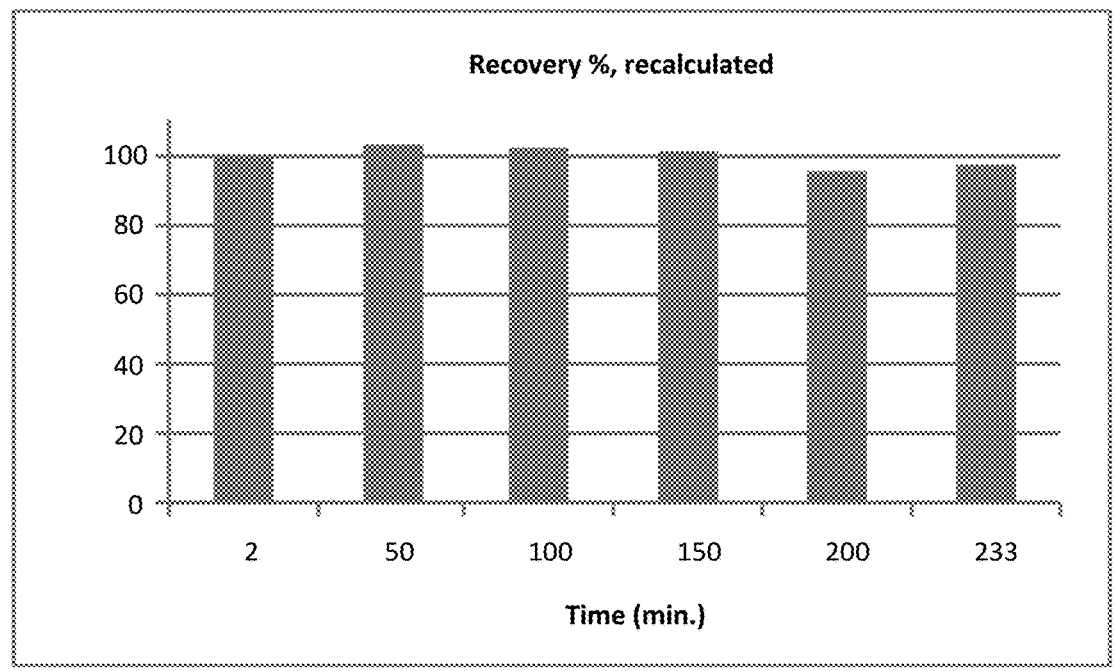
FIG. 14 shows the percent recovery of EPA+DHA at different time-points for preconcentrate D.
Figure 17:
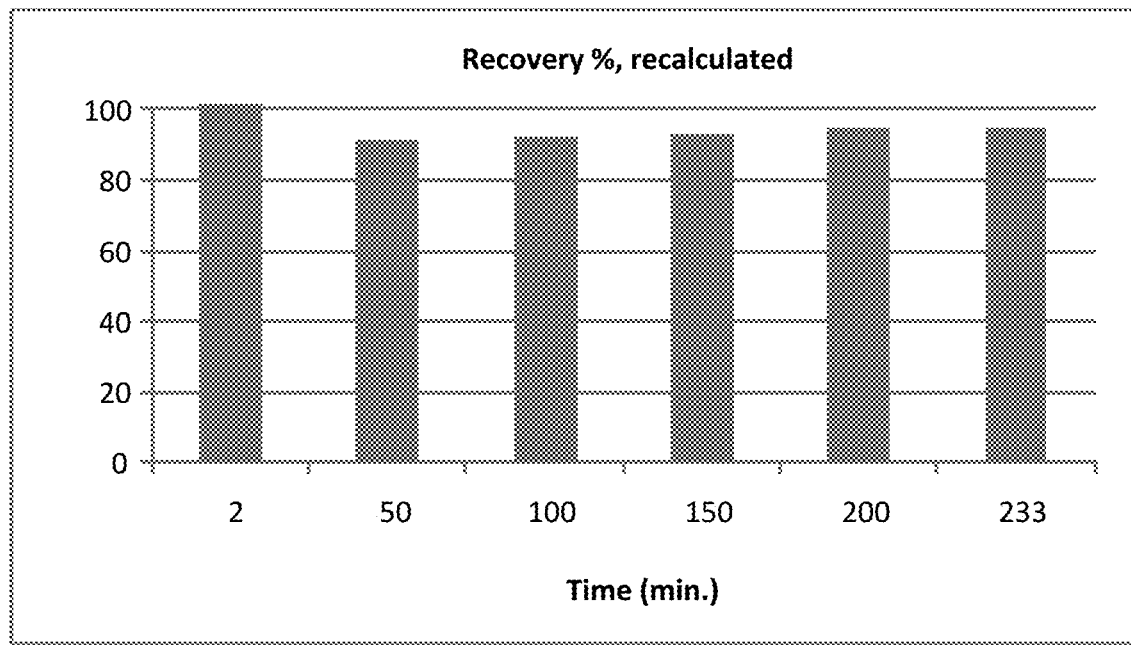
FIG. 17 shows the percent recovery of EPA+DHA at different time-points for preconcentrate E.

FIGS. 2, 5, 8, 11, 14, and 17 provide the percent recover of EPA+DHA at different time-points for each respective sample examined. Data are given as the sum of EPA-EE, DHA-EE, EPA-FA, and DHA-FA and given as a percentage of theoretical amount 5580 µg/ml.

Figure 6:
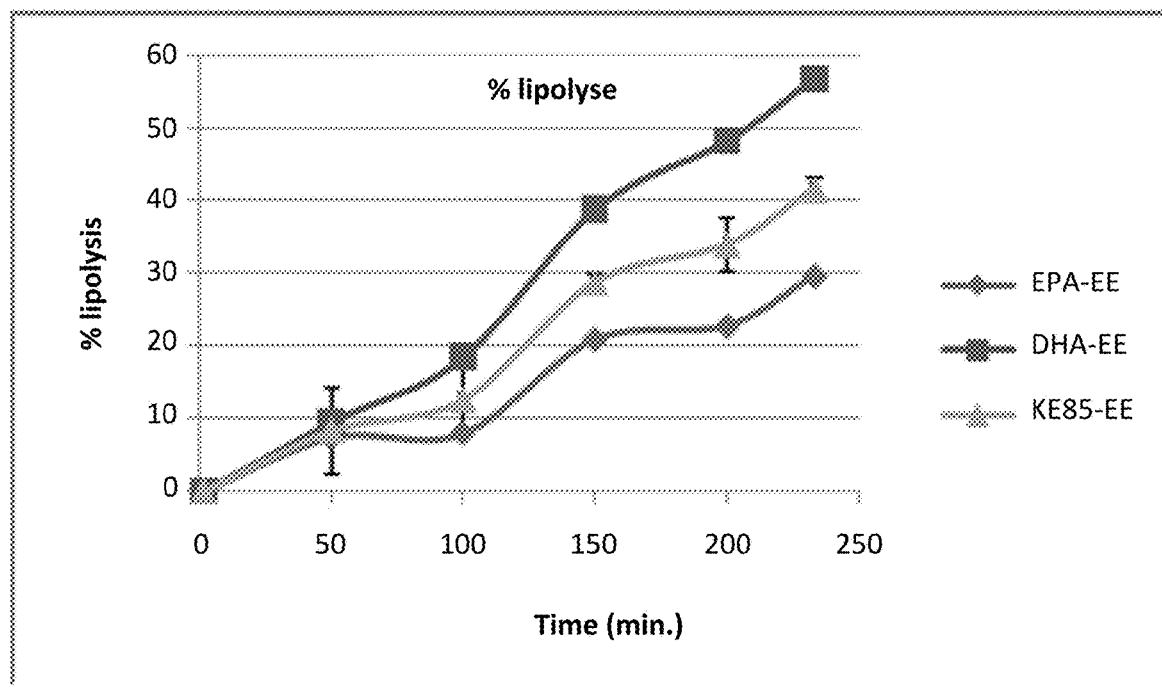
FIG. 6 shows the percent lipolysis of EPA-EE, DHA-EE and total K85EE at different time points for preconcentrate A.
Figure 9:
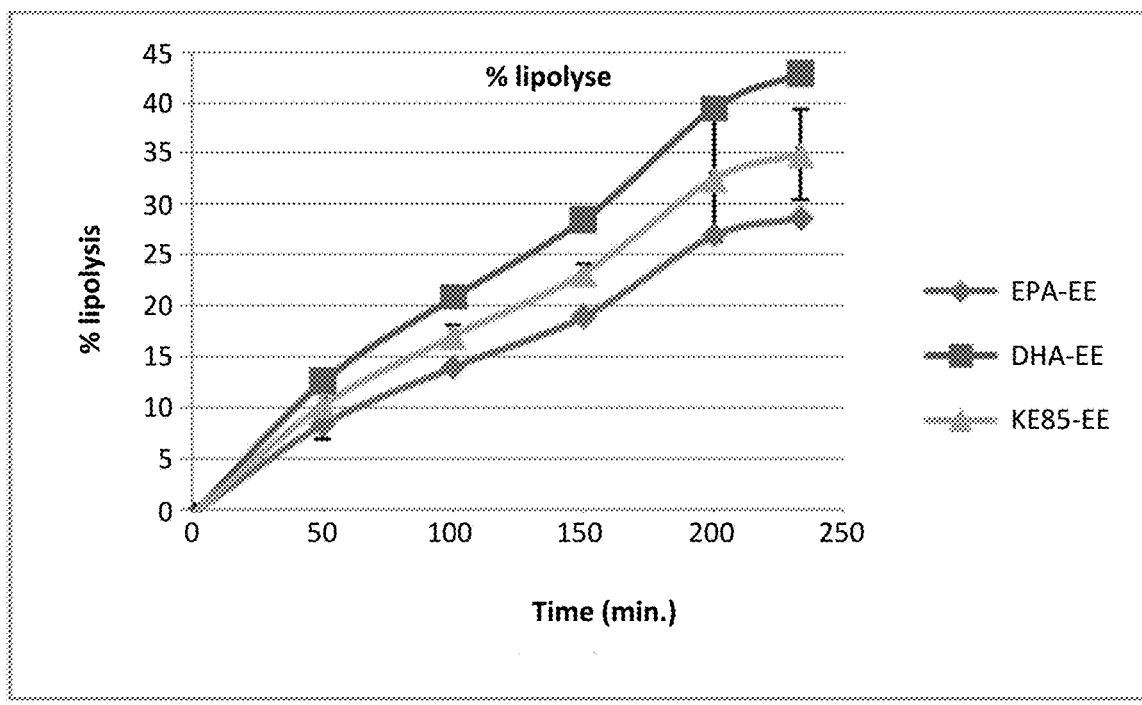
FIG. 9 shows the percent lipolysis of EPA-EE, DHA-EE and total K85EE at different time points for preconcentrate B.
Figure 12:
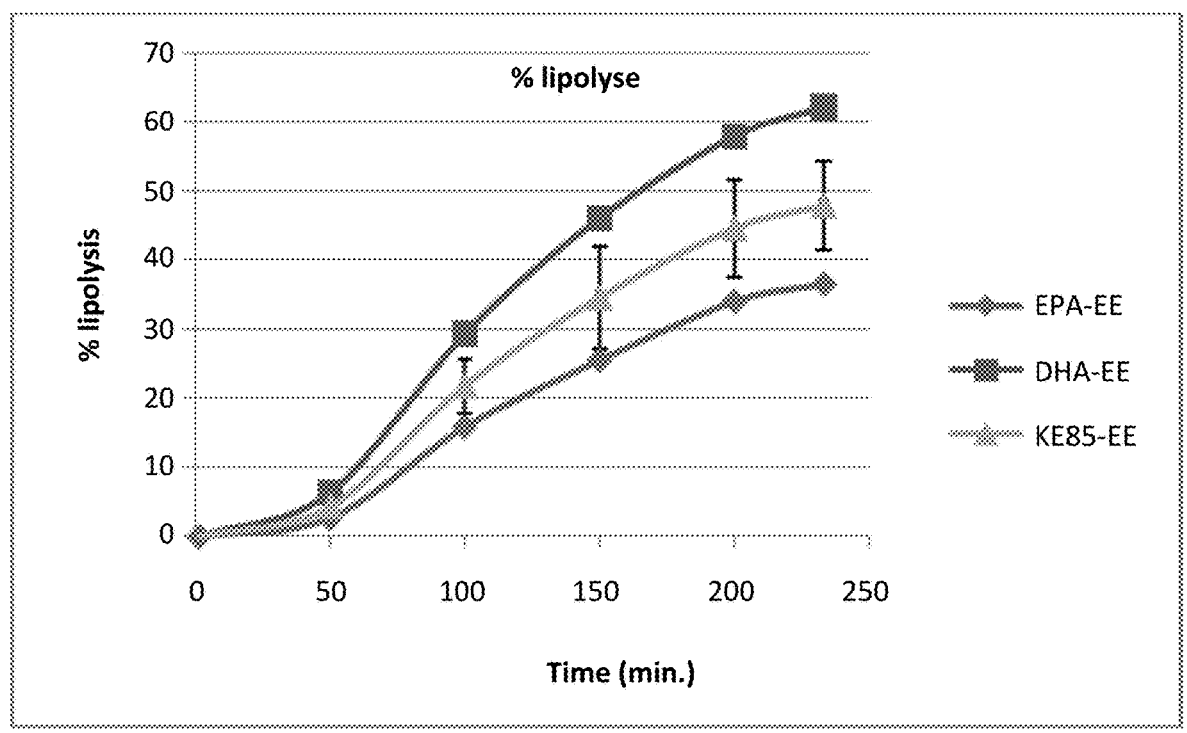
FIG. 12 shows the percent lipolysis of EPA-EE, DHA-EE and total K85EE at different time points for preconcentrate C.
Figure 13:
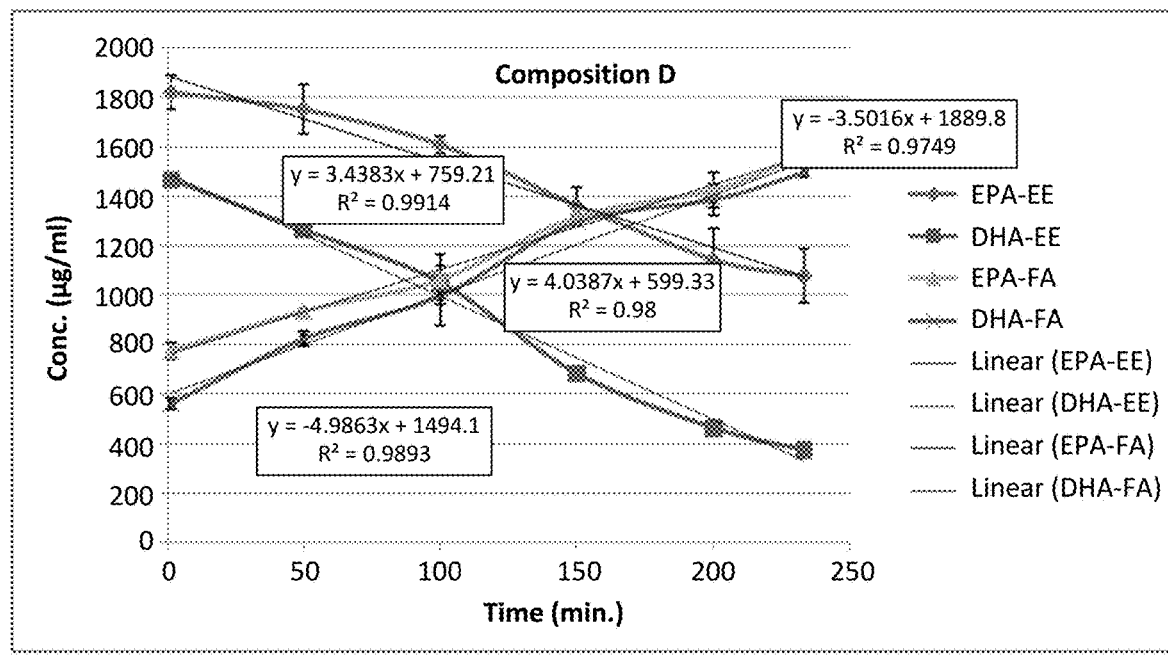
FIG. 13 shows the disappearance of EPA-EE and DHA-EE and the appearance of EPA-FA and DHA-FA during lipolysis of preconcentrate D.
Figure 15:
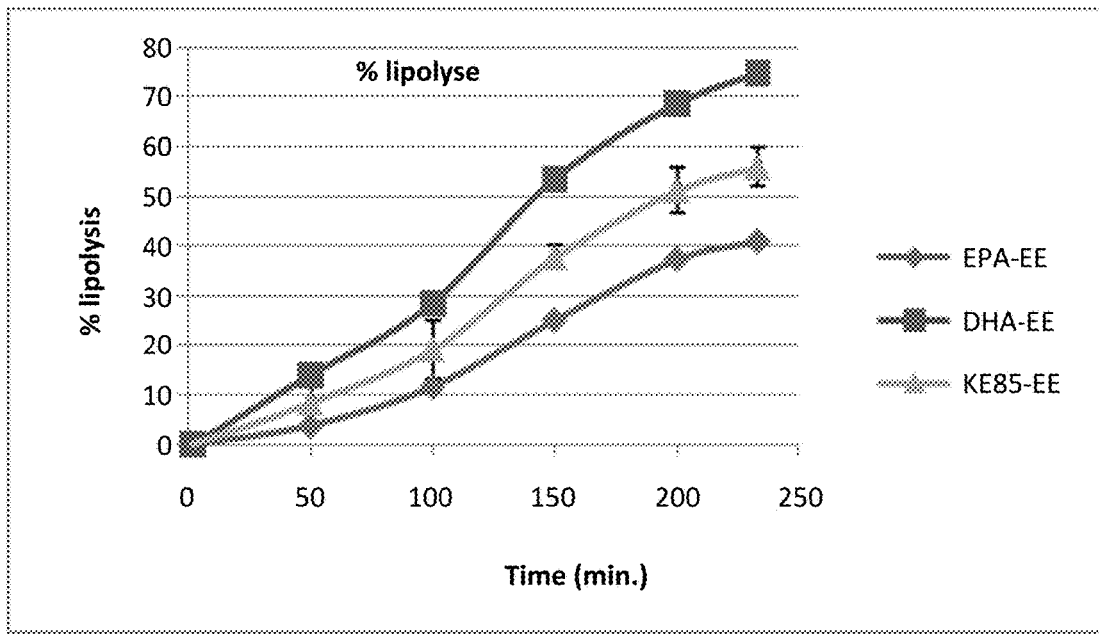
FIG. 15 shows the percent lipolysis of EPA-EE, DHA-EE and total K85EE at different time points for preconcentrate D.
Figure 18:
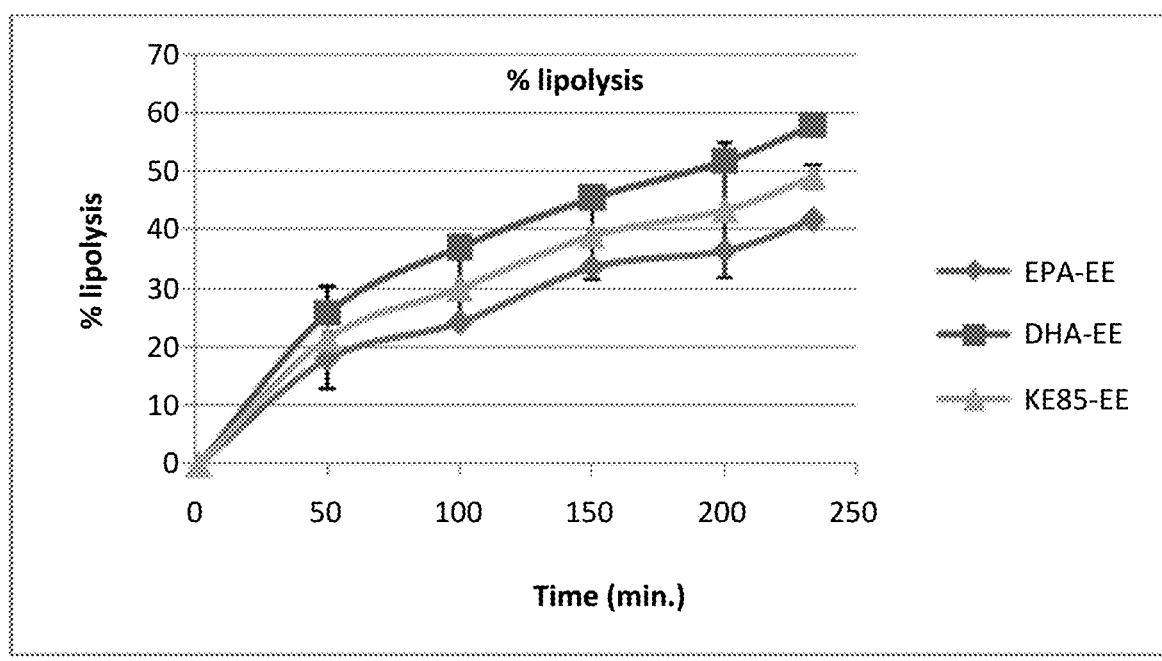
FIG. 18 shows the percent lipolysis of EPA-EE, DHA-EE and total K85EE at different time points for preconcentrate E.

FIGS. 3, 6, 9, 12, 15, and 18 graphically illustrate the percent lipolysis at different time points for EPA-EE, DHA-EE and total K85EE. Values are calculated relative to the total amount of EPA-EE and DHA-EE determined by HPLC after lipolysis for 2 minutes.

Example 3

Emulsions in Pure Water

The oil content in one capsule OMACOR®, comprising EPA ethyl ester (465 mg), DHA ethyl ester (375 mg) and alpha-tochopherol (4 mg) were mixed in a scintillation vial with various surfactants as shown below in Table 12. Water (10 ml) was added at 37 degrees centigrade and the mixture was shaken for 15 seconds using a Vortex mixer. The mixture was observed after 1 minute and after 5 minutes. The visual score for emulsion homogeneity was scored as follows: No emulsion=score 0, emulsion but not homogeneous emulsion=score 1, homogenous emulsion=score 2.

The mixture was after mixing also rolled in a roller mixer for 5 minutes. The visual score for this roller test was the same as above.

TABLE 12

Emulsions in pure water.

| Reference No. | Surfactant(s) | Amount of Surfactant (mg) | Score After Vortex for 1 minute | Score After Vortex 5 minutes | Score Roller Mixer |
|---|---|---|---|---|---|
| 1 | None | 0 | 0 | 0 | 0 |
| 2 | Brij ® 30 | 100 | 2 | 2 | 2 |
| 3 | Brij ® 35 | 100 | 2 | 1 | 2 |
| 4 | Brij ® 52 | 100 | 2 | 2 | 2 |
| 5 | Brij ® 58 | 100 | 2 | 1 | 2 |
| 6 | Brij ® 72 | 100 | 2 | 1 | 2 |
| 7 | Brij ® 78 | 100 | 2 | 1 | 2 |
| 8 | Brij ® 92V | 100 | 2 | 2 | 2 |
| 9 | Brij ® 93 | 100 | 2 | 2 | 2 |
| 10 | Brij ® 96V | 100 | 2 | 2 | 2 |
| 11 | Brij ® 97 | 100 | 2 | 2 | 2 |
| 12 | Brij ® 98 | 100 | 2 | 1 | 2 |
| 13 | Brij ® 700 | 100 | 1 | 1 | 2 |
| 14 | Brij ® S-10 | 100 | 1 | 1 | 2 |
| 15 | Pluronic ® L-31 | 100 | 1 | 1 | 2 |
| 16 | Pluronic ® L-35 | 100 | 1 | 1 | 2 |
| 17 | Pluronic ® L-81 | 100 | 2 | 2 | 2 |
| 18 | Pluronic ® L-64 | 100 | 2 | 2 | 2 |
| 19 | Pluronic ® L-121 | 100 | 2 | 2 | 2 |
| 20 | Pluronic ® P-123 | 100 | 1 | 1 | 2 |
| 21 | Pluronic ® F-68 | 100 | 0 | 0 | 1 |
| 22 | Pluronic ® F-108 | 100 | 0 | 0 | 1 |
| 23 | Span ® 20 | 100 | 2 | 2 | 2 |
| 24 | Span ® 60 | 100 | 0 | 0 | 1 |
| 25 | Span ® 65 | 100 | 0 | 0 | 0 |
| 26 | Span ® 80 | 100 | 1 | 1 | 2 |
| 27 | Span ® 85 | 100 | 0 | 0 | 1 |
| 28 | Tween ® 20 | 100 | 2 | 1 | 2 |
| 29 | Tween ® 40 | 100 | 2 | 1 | 2 |
| 30 | Tween ® 60 | 100 | 2 | 1 | 2 |
| 31 | Tween ® 80 | 100 | 2 | 1 | 2 |
| 32 | Alginic Acid | 100 | 1 | 0 | 1 |
| 33 | Alginic Acid sodium salt | 100 | 2 | 1 | 1 |
| 34 | Macrogolglycerol-hydroxystearas 40 | 100 | 2 | 2 | 2 |
| 35 | Sodium lauryl sulphate | 100 | 1 | 1 | 2 |
| 36 | 1,2-Dipalmitoyl-sn-glycerol ethanolamine | 100 | 0 | 0 | 0 |
| 37 | 1-Hexadecanol | 100 | 1 | 0 | 0 |
| 38 | 1,2-Dipalmitoy-sn | 100 | 2 | 1 | 1 |
| 39 | Macrogol 400 | 100 | 0 | 0 | 1 |
| 40 | Myristic acid sodium salt | 100 | 1 | 1 | 1 |
| 41 | Brij ® 52/ Macrogolglycerol-hydroxystearas 40 | 30/20 | 2 | 2 | 2 |

TABLE 12-continued

Emulsions in pure water.

| Reference No. | Surfactant(s) | Amount of Surfactant (mg) | Score After Vortex for 1 minute | Score After Vortex 5 minutes | Score Roller Mixer |
|---|---|---|---|---|---|
| 42 | Brij ® 62/ Pluronic ® L64 | 30/50 | 2 | 2 | 2 |
| 43 | Span ® 20/ Pluronic ® L64 | 40/90 | 2 | 2 | 2 |
| 44 | Macrogol 400/ Macrogol-glycerol-hydroxystearas 40 | 120/60 | 2 | 2 | 2 |
| 45 | Tween ® 20/ Span ® 20 | 60/60 | 2 | 2 | 2 |
| 46 | Tween ® 20/ Span ® 20/ Macrogol 400 | 90/90/60 | 2 | 2 | 2 |
| 47 | Span ® 20/ Tween ® 20/ Brij ® 97 | 70/100/40 | 2 | 2 | 2 |
| 48 | Alginic acid sodium salt/Span ® 60 | 110/60 | 2 | 2 | 2 |
| 49 | Pluronic ® F-68/ Pluronic ® L64/ Span ® 60 | 20/180/20 | 2 | 2 | 2 |

Example 4

Emulsions in Artificial Gastric Juice

The oil content in one capsule OMACOR®, comprising EPA ethyl ester (465 mg), DHA ethyl ester (375 mg) and alpha-tochopherol (4 mg) were mixed in a scintillation vial with various surfactants as shown below in Table 13. The experimental set up in the examples below is the same as described previously except that that artificial gastric juice without pepsin (European Pharmacopeia 6.0, page 274) was used instead of water.

TABLE 13

Emulsions in artificial gastric juice

| Reference No. | Surfactant(s) | Amount of Surfactant (mg) | Score After Vortex for 1 minute | Score after Vortex for 5 minutes | Score Roller Mixer |
|---|---|---|---|---|---|
| 50 | None | 0 | 0 | 0 | 0 |
| 51 | Brij ® 52 | 100 | 2 | 1 | 2 |
| 52 | Brij ® 96V | 100 | 2 | 1 | 2 |
| 53 | Pluronic ® L64 | 100 | 2 | 2 | 2 |
| 54 | Tween ® 40 | 100 | 2 | 2 | 2 |
| 55 | Macrogolglycerol-Hydroxysteraras 40 | 100 | 2 | 2 | 2 |

Example 5

Emulsions in Simulated Intestinal Fluid

The oil content in one capsule OMACOR®, comprising EPA ethyl ester (465 mg), DHA ethyl ester (375 mg) and alpha-tochopherol (4 mg) were mixed in a scintillation vial with various surfactants as shown below in Table 14. The experimental set up in the examples below is the same as described previously except that that simulated intestinal fluid pH 6.8 without pancreas powder (European Pharmacopeia 6.0, page 274) was used instead of water.

TABLE 14

Emulsions in simulated intestinal fluid.

| Reference No. | Surfactant(s) | Amount of Surfactant (mg) | Score After Vortex for 1 minute | Score after Vortex for 5 minutes | Score Roller Mixer |
|---|---|---|---|---|---|
| 56 | None | 0 | 0 | 0 | 0 |
| 57 | Brij ® 52 | 100 | 2 | 2 | 2 |
| 58 | Brij ® 96V | 100 | 2 | 2 | 2 |
| 59 | Pluronic ® L64 | 100 | 2 | 2 | 2 |
| 60 | Tween ® 40 | 100 | 2 | 2 | 2 |
| 61 | Macrogolglycerol-Hydroxysteraras 40 | 100 | 2 | 2 | 2 |

Example 6

Microscopic Examination of Emulsions

Emulsions from Example 52 (gastric juice) and Example 58 (intestinal fluid) were examined under the microscope after 24 hours rolling. Both emulsions were found to be suspensions of oil in water with no tendency to aggregation.

Example 7

Pharmaceutical Formulations

The following examples in Table 15 illustrate pharmaceutical formulations that can be prepared.

TABLE 15

Pharmaceutical Formulations

| Example No. | K85EE or AGP103 Oil Mixture | Surfactant or Surfactant System |
|---|---|---|
| 64 | X | Tween ® 20 |
| 65 | X | Tween ® 40 |
| 66 | X | Tween ® 80 |
| 67 | X | Tween ® 20 + Tween ® 40 |
| 68 | X | Tween ® + Cremphor ® |
| 69 | X | Tween ® + Solutol HS 15 |

In an embodiment, the surfactant or combination of surfactants is chosen from Tween® surfactants; Tween® 20, Tween® 40, Tween® 60, Tween® 65, Tween® 80 and Tween® 85.

In another embodiment, the surfactant is chosen from a combination of a Tween® surfactants and a surfactant chosen from Cremphor®, for instance Tween® 20 and Cremphor EL. Moreover, in a further embodiment, a Tween® 20 and Solutol HS 15 surfactant can be used together as well as Tween® 20 and Tween® 40.

Fatty acid oil mixtures of pharmaceutical preconcentrates, wherein the fatty acid oil mixture is a K85EE or AGP-103 oil composition are presented in Table 16.

TABLE 16

Fatty acid oil mixture for pharmaceutical preconcentrates.

| Fatty acid oil mixture: 1000 mg K85EE fatty acid oil mixture | Minimum Value | Maximum Value |
|---|---|---|
| EPAEE + DHAEE | 800 mg/g | 880 mg/g |
| EPAEE | 430 mg/g | 495 mg/g |

TABLE 16-continued

Fatty acid oil mixture for pharmaceutical preconcentrates.

| Fatty acid oil mixture:<br>1000 mg K85EE fatty<br>acid oil mixture | Minimum Value | Maximum Value |
|---|---|---|
| DHAEE | 347 mg/g | 403 mg/g |
| Total omega-3 EE | >90% (w/w) | |

EE = ethyl ester

Example 8

Additional Emulsions in Artificial Gastric Juice and Simulated Intestinal Fluid

Preconcentrates 1-23 were prepared with EPA/DHA ethyl ester (1000 mg K85EE) and various surfactants and surfactant mixtures as shown in Table 17 below. Emulsions were prepared in both gastric juice and simulated intestinal fluid as described in Examples 4 and 5. Results were the same for emulsions in artificial gastric juice and simulated intestinal fluid, and appear in Table 17.

TABLE 17

Emulsions in artificial gastric juice and simulated intestinal fluid.

| Reference No. | Surfactant(s) | Amount of Surfactant (mg) | Score After Vortex for 1 minute | Score After Vortex 5 minutes | Score Roller Mixer |
|---|---|---|---|---|---|
| 1 | Cremophor ® EL | 20 | 2 | 1 | 2 |
| 2 | Cremophor ® EL | 80 | 2 | 1 | 2 |
| 3 | Cremophor ® EL | 100 | 2 | 1 | 2 |
| 4 | Cremophor ® EL | 150 | 2 | 2 | 2 |
| 5 | Cremophor ® EL | 200 | 2 | 2 | 2 |
| 6 | Cremophor ® EL | 250 | 2 | 2 | 2 |
| 7 | Cremophor ® EL | 300 | 2 | 2 | 2 |
| 8 | Cremophor ® EL | 400 | 2 | 2 | 2 |
| 9 | Cremophor ® EL | 500 | 2 | 2 | 2 |
| 10 | Cremophor ® EL | 600 | 2 | 2 | 2 |
| 11 | Cremophor ® EL | 700 | 2 | 2 | 2 |
| 12 | Cremophor ® EL | 800 | 2 | 2 | 2 |
| 13 | Cremophor ® EL | 900 | 2 | 2 | 2 |
| 14 | Cremophor ® EL | 1000 | 2 | 2 | 2 |
| 15 | Cremophor ® EL | 1200 | 2 | 2 | 2 |
| 16 | Cremophor ® EL<br>Tween ® 60 | 150<br>100 | 2 | 2 | 1 |
| 17 | Cremophor ® EL<br>Brij ® 30<br>Span ® 85 | 40<br>20<br>20 | 2 | 2 | 2 |
| 18 | Cremophor ® EL | 5 | 2 | 1 | 2 |
| 19 | Cremophor ® EL<br>Tween ® 80 | 60<br>70 | 2 | 1 | 2 |
| 20 | Macrogolglyceroli Hydroxystearas 40 | 60 | 2 | 1 | 2 |
| 21 | Macrogolglyceroli Hydroxystearas 40<br>Span ® 20<br>Polysorbate 20 | 90<br>30<br>50 | 2 | 1 | 2 |
| 22 | Macrogolglyceroli Hydroxystearas 40<br>Brij ® 93<br>Polysorbate 20 | 60<br>30<br>60 | 2 | 1 | 2 |
| 23 | Cremophor ® EL<br>Pluronic ® F68<br>Brij ® 92V<br>Polysorbate 20 | 60<br>30<br>30<br>20 | 2 | 2 | 2 |

Emulsions 4-15 prepared in both artificial gastric juice and simulated intestinal fluid were homogenous (milky) for several hours when standing. Emulsions 1-3 separated somewhat after preparation (i.e., after several hours of standing). Microscopy of Emulsions 1-15 showed that the average particle size was less than 100 micrometers. Homogenization treatment (UltraRurrax(IKA)) of Emulsion 4 for 20 seconds resulted in a substantial increase of formation of small particles (<10 microns).

Based on the preconcentrates prepared, a 0.5% non-ionic surfactant (e.g., Cremophor®) can emulsify EPA/DHA ethyl ester in both artificial gastric juice and simulated intestinal fluid. In addition, including more than one surfactant appears to stabilize the emulsion. Further, the particle size can vary depending upon the emulsification method.

What is claimed is:

1. A preconcentrate comprising:
    a fatty acid oil mixture comprising at least 75% eicosapentaenoic acid (EPA) and docosahexaenoic acid (DHA), by weight of the fatty acid oil mixture, wherein the EPA and DHA are in a form chosen from ethyl ester and triglyceride; and
    from about 0.5% to about 40% of at least one nonionic surfactant chosen from polysorbate 20, polysorbate 80, and mixtures thereof,
    by weight relative to the total weight of the preconcentrate, wherein the at least one nonionic surfactant enhances lipolysis of EPA and DHA ethyl esters; and
    wherein the preconcentrate does not comprise a pharmaceutically active agent other than the fatty acid oil mixture.

2. The preconcentrate according to claim 1, wherein of the at least 75% EPA and DHA of the fatty acid oil mixture, at least 95% is EPA.

3. The preconcentrate according to claim 1, wherein of the at least 75% EPA and DHA of the fatty acid oil mixture, at least 95% is DHA.

4. The preconcentrate according to claim 1, wherein the fatty acid oil mixture comprises at least 90% omega-3 fatty acids, by weight of the fatty acid oil mixture.

5. The preconcentrate according to claim 4, wherein at least one of the omega-3 fatty acids has a cis configuration.

6. The preconcentrate according to claim 1, wherein the fatty acid oil mixture further comprises at least one other fatty acid other than EPA and DHA chosen from α-linolenic acid (ALA), heneicosapentaenoic acid (HPA), docosapentaenoic acid (DPA), eicosatetraenoic acid (ETA), eicosatrienoic acid (ETE), stearidonic acid (STA), linoleic acid, gamma-linolenic acid (GLA), arachidonic acid (AA), osbond acid, and mixtures thereof.

7. The preconcentrate according to claim 1, wherein the fatty acid oil mixture is derived from at least one oil chosen from marine oil, algae oil, plant-based oil, and microbial oil.

8. The preconcentrate according to claim 7, wherein the marine oil is a purified fish oil.

9. The preconcentrate according to claim 1, wherein the EPA:DHA weight ratio of the fatty acid oil mixture ranges from about 1:10 to 10:1.

10. The preconcentrate according to claim 1, wherein the preconcentrate comprises from about 10% to about 30% of the at least one nonionic surfactant, by weight relative to the total weight of the preconcentrate.

11. The preconcentrate according to claim 10, wherein the preconcentrate comprises about 20% of the at least one nonionic surfactant, by weight relative to the total weight of the preconcentrate.

12. The preconcentrate according to claim 1, further comprising at least one co-surfactant chosen from short chain alcohols, glycol ethers, pyrrolidine derivatives, 2-pyrrolidone, bile salts, and mixtures thereof.

13. The preconcentrate according to claim 12, wherein the preconcentrate comprises from about 1% to about 10% of the at least one co-surfactant, by weight relative to the total weight of the preconcentrate.

14. The preconcentrate according to claim 1, wherein the weight ratio of fatty acid oil mixture:total surfactant ranges from about 1:1 to about 200:1.

15. The preconcentrate according to claim 1, wherein the preconcentrate further comprises at least one pharmaceutically-acceptable solvent chosen from lower alcohols and polyols.

16. The preconcentrate according to claim 1, further comprising at least one antioxidant in an amount less than a pharmaceutically-effective amount.

17. The preconcentrate according to claim 16, wherein the at least one antioxidant is chosen from butylhydroxyanisoles (BHA) and α-tocopherol.

18. The preconcentrate according to claim 1, wherein the fatty acid oil mixture is present in a pharmaceutically-effective amount.

19. The preconcentrate according to claim 1, wherein the preconcentrate is in the form of a gelatin capsule.

20. The preconcentrate according to claim 19, wherein the capsule fill content ranges from about 0.400 g to about 1.300 g.

21. The preconcentrate according to claim 1, wherein the fatty acid oil mixture comprises from about 80% to about 88% EPA and DHA, by weight of the fatty acid oil mixture, wherein the EPA and DHA are in ethyl ester form.

22. The preconcentrate according to claim 21, further comprising
at least one co-surfactant comprising ethanol.

23. A self-nanoemulsifying drug delivery system (SNEDDS), self-microemulsifying drug delivery system (SMEDDS), or self-emulsifying drug delivery system (SEDDS) comprising a preconcentrate comprising:
a fatty acid oil mixture comprising from about 80% to about 88% eicosapentaenoic acid (EPA) and docosahexaenoic acid (DHA), by weight of the fatty acid oil mixture, wherein the EPA and DHA are in a form chosen from ethyl ester and triglyceride; and
from about 0.5% to about 40% of at least one nonionic surfactant chosen from polysorbate 20, polysorbate 80, and mixtures thereof,
by weight relative to the total weight of the preconcentrate, wherein the at least one nonionic surfactant enhances lipolysis of EPA and DHA ethyl esters;
wherein the preconcentrate forms an emulsion in an aqueous solution; and
wherein the preconcentrate does not comprise a pharmaceutically active agent other than the fatty acid oil mixture.

24. The system according to claim 23, wherein the fatty acid oil mixture comprises at least 90% omega-3 fatty acids, by weight of the fatty acid oil mixture.

25. The system according to claim 24, wherein at least one of the omega-3 fatty acids has a cis configuration.

26. The system according to claim 23, wherein the fatty acid oil mixture further comprises at least one other fatty acid other than EPA and DHA chosen from α-linolenic acid (ALA), heneicosapentaenoic acid (HPA), docosapentaenoic acid (DPA), eicosatetraenoic acid (ETA), eicosatrienoic acid (ETE), stearidonic acid (STA), linoleic acid, gamma-linolenic acid (GLA), arachidonic acid (AA), osbond acid, and mixtures thereof.

27. The system according to claim 23, wherein the fatty acid oil mixture is derived from at least one oil chosen from marine oil, algae oil, plant-based oil, and microbial oil.

28. The system according to claim 27, wherein the marine oil is a purified fish oil.

29. The system according to claim 23, wherein the EPA:DHA weight ratio of the fatty acid oil mixture ranges from about 1:10 to 10:1.

30. The system according to claim 23, wherein the preconcentrate comprises from about 10% to about 30% of the at least one nonionic surfactant, by weight relative to the total weight of the preconcentrate.

31. The system according to claim 30, wherein the preconcentrate comprises about 20% of the at least one nonionic surfactant, by weight relative to the total weight of the preconcentrate.

32. The system according to claim 23, wherein the preconcentrate further comprises at least one co-surfactant chosen from short chain alcohols, glycol ethers, pyrrolidine derivatives, 2-pyrrolidone, bile salts, and mixtures thereof.

33. The system according to claim 32, wherein the preconcentrate comprises from about 1% to about 10% of the at least one co-surfactant, by weight relative to the total weight of the preconcentrate.

34. The system according to claim 23, wherein the weight ratio of fatty acid oil mixture:total surfactant ranges from about 1:1 to about 200:1.

35. The system according to claim 23, wherein the preconcentrate further comprises at least one pharmaceutically-acceptable solvent chosen from lower alcohols and polyols.

36. The system according to claim 23, wherein the preconcentrate further comprises at least one antioxidant in an amount less than a pharmaceutically-effective amount.

37. The system according to claim 36, wherein the at least one antioxidant is chosen from butylhydroxyanisoles (BHA) and α-tocopherol.

38. The system according to claim 23, wherein the fatty acid oil mixture is present in a pharmaceutically-effective amount.

39. The system according to claim 23, wherein the system is in the form of a gelatin capsule.

40. The system according to claim 39, wherein the capsule fill content ranges from about 0.400 g to about 1.300 g.

41. The system according to claim 23, wherein the particle size of the emulsion ranges from about 150 nm to about 350 nm.

42. A method of treating at least one health problem in a subject in need thereof comprising administering to the subject a pharmaceutical preconcentrate comprising:
a fatty acid oil mixture comprising at least 75% eicosapentaenoic acid (EPA) and docosahexaenoic acid (DHA), by weight of the fatty acid oil mixture, wherein the EPA and DHA are in a form chosen from ethyl ester and triglyceride; and
at least one nonionic surfactant chosen from polysorbate 20, polysorbate 80, and mixtures thereof;
wherein the pharmaceutical preconcentrate does not comprise a pharmaceutically active agent other than the fatty acid oil mixture; and
wherein the at least one health problem is chosen from cardiovascular functions, immune functions, visual functions, insulin action, neuronal development, heart failure, post myocardial infarction, mixed dyslipidemia, dyslipidemia, hypertriglyceridemia, and hypercholesterolemia.

43. The method according to claim 42, wherein the at least one health problem is chosen from elevated triglyceride levels, non-HDL cholesterol levels, LDL cholesterol levels and/or VLDL cholesterol levels.

44. The method according to claim 42, wherein the fatty acid oil mixture comprises at least 90% omega-3 fatty acids, by weight of the fatty acid oil mixture.

45. The method according to claim 44, wherein at least one of the omega-3 fatty acids has a cis configuration.

46. The method according to claim 42, wherein the fatty acid oil mixture further comprises at least one other fatty acid other than EPA and DHA chosen from α-linolenic acid (ALA), heneicosapentaenoic acid (HPA), docosapentaenoic acid (DPA), eicosatetraenoic acid (ETA), eicosatrienoic acid (ETE), stearidonic acid (STA), linoleic acid, gamma-linolenic acid (GLA), arachidonic acid (AA), osbond acid, and mixtures thereof.

47. The method according to claim 42, wherein the fatty acid oil mixture is derived from at least one oil chosen from marine oil, algae oil, plant-based oil, and microbial oil.

48. The method according to claim 47, wherein the marine oil is a purified fish oil.

49. The method according to claim 42, wherein the EPA:DHA weight ratio of the fatty acid oil mixture ranges from about 1:10 to 10:1.

50. The method according to claim 42, wherein the preconcentrate further comprises at least one co-surfactant chosen from short chain alcohols, glycol ethers, pyrrolidine derivatives, 2-pyrrolidone, bile salts, and mixtures thereof.

51. The method according to claim 42, wherein the preconcentrate further comprises at least one antioxidant in an amount less than a pharmaceutically effective amount.

52. The method according to claim 42, wherein the preconcentrate is in the form of a gelatin capsule.

53. The method according to claim 52, wherein the capsule fill content ranges from about 0.400 g to about 1.300 g.

54. The method according to claim 42, wherein the preconcentrate is administered once per day.

55. The method according to claim 42, wherein the preconcentrate forms a self-nanoemulsifying drug delivery system (SNEDDS), self-microemulsifying drug delivery system (SMEDDS), or self-emulsifying drug delivery system (SEDDS) in an aqueous solution.

56. A preconcentrate comprising:
a fatty acid oil mixture comprising from about 25% to about 75% eicosapentaenoic acid (EPA) and docosahexaenoic acid (DHA), by weight of the fatty acid oil mixture, wherein the EPA and DHA are in a form chosen from ethyl ester and triglyceride; and
from about 0.5% to about 40% of at least one nonionic surfactant chosen from polysorbate 20, polysorbate 80, and mixtures thereof,
by weight relative to the total weight of the preconcentrate, wherein the at least one nonionic surfactant enhances lipolysis of EPA and DHA ethyl esters;
wherein the preconcentrate does not comprise a pharmaceutically active agent other than the fatty acid oil mixture.

57. The preconcentrate according to claim 56, wherein the fatty acid oil mixture comprises from about 35% to about 75% EPA and DHA.

58. The preconcentrate according to claim 56, wherein the fatty acid oil mixture is derived from at least one oil chosen from marine oil, algae oil, plant-based oil, and microbial oil.

59. The preconcentrate according to claim 58, wherein the marine oil is a purified fish oil.

60. The preconcentrate according to claim 56, wherein the EPA:DHA weight ratio of the fatty acid oil mixture ranges from about 1:10 to about 10:1.

61. The preconcentrate according to claim 56, further comprising at least one co-surfactant chosen from short chain alcohols, glycol ethers, pyrrolidine derivatives, 2-pyrrolidone, bile salts, and mixtures thereof.

62. The preconcentrate according to claim 56, further comprising at least one antioxidant in an amount less than a pharmaceutically effective amount.

63. The preconcentrate according to claim 56, wherein the preconcentrate is in the form of a gelatin capsule.

64. The preconcentrate according to claim 63, wherein the capsule fill content ranges from about 0.400 g to about 1.300 g.

65. The preconcentrate according to claim 56, wherein the preconcentrate forms a self-nanoemulsifying drug delivery system (SNEDDS), self-microemulsifying drug delivery system (SMEDDS), or self-emulsifying drug delivery system (SEDDS) in an aqueous solution.

66. A method for enhancing at least one parameter chosen from hydrolysis, solubility, bioavailability, absorption, and combinations thereof of eicosapentaenoic acid (EPA) and docosahexaenoic acid (DHA) comprising combining:
a fatty acid oil mixture comprising EPA and DHA in a form chosen from ethyl ester and triglyceride; and
at least one nonionic surfactant chosen from polysorbate 20, polysorbate 80, and mixtures thereof;
wherein the fatty acid oil mixture and the at least one nonionic surfactant form a preconcentrate; and
wherein the preconcentrate does not comprise a pharmaceutically active agent other than the fatty acid oil mixture.

67. The method according to claim 66, wherein the fatty acid oil mixture comprises at least 75% eicosapentaenoic acid (EPA) and docosahexaenoic acid (DHA), by weight of the fatty acid oil mixture.

68. The method according to claim 66, wherein the fatty acid oil mixture comprises from about 25% to about 75% eicosapentaenoic acid (EPA) and docosahexaenoic acid (DHA), by weight of the fatty acid oil mixture.

69. The method according to claim 66, wherein the preconcentrate further comprises at least one co-surfactant chosen from short chain alcohols, glycol ethers, pyrrolidine derivatives, 2-pyrrolidone, bile salts, and mixtures thereof.

70. The method according to claim 67, wherein the fatty acid oil mixture comprises from about 80% to about 88% eicosapentaenoic acid (EPA) and docosahexaenoic acid (DHA), by weight of the fatty acid oil mixture.

71. The method according to claim 70, wherein the preconcentrate further comprises
at least one co-surfactant comprising ethanol.

72. The method according to claim 66, wherein the preconcentrate forms a self-nanoemulsifying drug delivery system (SNEDDS), self-microemulsifying drug delivery system (SMEDDS), or self-emulsifying drug delivery system (SEDDS) in an aqueous solution.

73. The method according to claim 72, wherein the system comprises an emulsion with a particle size ranging from about 150 nm to about 350 nm.

74. The preconcentrate of claim 1, further comprising:
at least one free fatty acid chosen from oleic acid and linoleic acid; and
at least one antioxidant in an amount less than a pharmaceutically effective amount.

75. The preconcentrate of claim 74, wherein:
the fatty acid oil mixture comprises about 84% EPA and DHA, by weight of the fatty acid oil mixture;
the at least one nonionic surfactant comprises polysorbate 20; and
the at least one free fatty acid comprises oleic acid.

76. The preconcentrate of claim 1, wherein the preconcentrate further comprises at least one co-surfactant chosen from short chain alcohols.

77. The preconcentrate of claim 56, wherein the preconcentrate further comprises at least one co-surfactant chosen from short chain alcohols.

78. The preconcentrate of claim 56, further comprising:
at least one free fatty acid chosen from oleic acid and linoleic acid; and
at least one antioxidant in an amount less than a pharmaceutically effective amount.

79. The preconcentrate of claim 78, wherein:
the at least one nonionic surfactant comprises polysorbate 20; and
the at least one free fatty acid comprises oleic acid.

80. The preconcentrate according to claim 56, wherein the fatty acid oil mixture further comprises at least one other fatty acid other than EPA and DHA chosen from α-linolenic acid (ALA), heneicosapentaenoic acid (HPA), docosapentaenoic acid (DPA), eicosatetraenoic acid (ETA), eicosatrienoic acid (ETE), stearidonic acid (STA), linoleic acid, gamma-linolenic acid (GLA), arachidonic acid (AA), osbond acid, and mixtures thereof.

81. The preconcentrate according to claim 56, wherein the fatty acid oil mixture comprises at least one other fatty acid other than EPA and DHA chosen from oleic acid, ricinoleic acid, erucic acid, and mixtures thereof.

82. The preconcentrate according to claim 1, wherein the fatty acid oil mixture comprises at least one other fatty acid other than EPA and DHA chosen from oleic acid, ricinoleic acid, erucic acid, and mixtures thereof.

83. The preconcentrate according to claim 23, wherein the fatty acid oil mixture comprises at least one other fatty acid other than EPA and DHA chosen from oleic acid, ricinoleic acid, erucic acid, and mixtures thereof.

84. The preconcentrate according to claim 42, wherein the fatty acid oil mixture comprises at least one other fatty acid other than EPA and DHA chosen from oleic acid, ricinoleic acid, erucic acid, and mixtures.

85. The preconcentrate according to claim 1, wherein the EPA:DHA weight ratio of the fatty acid oil mixture ranges from about 1:6 to 6:1.

86. The preconcentrate according to claim 1, wherein the EPA:DHA weight ratio of the fatty acid oil mixture ranges from about 1:3 to 3:1.

87. The preconcentrate according to claim 1, wherein the EPA:DHA weight ratio of the fatty acid oil mixture ranges from about 1:2 to 1:3.

88. The preconcentrate according to claim 1, wherein the preconcentrate comprises from about 10% to about 25% of the at least one nonionic surfactant, by weight relative to the total weight of the preconcentrate.

89. The preconcentrate according to claim 1, wherein the weight ratio of fatty acid oil mixture:total surfactant ranges from about 1:1 to about 50:1.

90. The preconcentrate according to claim 1, wherein the weight ratio of fatty acid oil mixture:total surfactant ranges from about 1:1 to 6:1.

91. The preconcentrate according to claim 1, wherein the weight ratio of fatty acid oil mixture:total surfactant ranges from about 1:1 to about 3:1.

92. The preconcentrate according to claim 19, wherein the capsule fill content ranges from about 0.600 g to about 1.200 g.

93. The preconcentrate according to claim 19, wherein the capsule fill content ranges from about 0.800 g to about 1.000 g.

94. The system according to claim 23, wherein the EPA:DHA weight ratio of the fatty acid oil mixture ranges from about 1:6 to 6:1.

95. The system according to claim 23, wherein the EPA:DHA weight ratio of the fatty acid oil mixture ranges from about 1:3 to 3:1.

96. The system according to claim 23, wherein the EPA:DHA weight ratio of the fatty acid oil mixture ranges from about 1:2 to 1:3.

97. The system according to claim 23, wherein the preconcentrate comprises from about 10% to about 25% of the at least one nonionic surfactant, by weight relative to the total weight of the preconcentrate.

98. The system according to claim 23, wherein the weight ratio of fatty acid oil mixture:total surfactant ranges from about 1:1 to about 50:1.

99. The system according to claim 23, wherein the weight ratio of fatty acid oil mixture:total surfactant ranges from about 1:1 to 6:1.

100. The system according to claim 23, wherein the weight ratio of fatty acid oil mixture:total surfactant ranges from about 1:1 to about 3:1.

101. The system according to claim 39, wherein the capsule fill content ranges from about 0.600 g to about 1.200 g.

102. The system according to claim 39, wherein the capsule fill content ranges from about 0.800 g to about 1.000 g.

103. The method according to claim 42, wherein the EPA:DHA weight ratio of the fatty acid oil mixture ranges from about 1:6 to 6:1.

104. The method according to claim 42, wherein the EPA:DHA weight ratio of the fatty acid oil mixture ranges from about 1:3 to 3:1.

105. The method according to claim 42, wherein the EPA:DHA weight ratio of the fatty acid oil mixture ranges from about 1:2 to 1:3.

106. The method according to claim 52, wherein the capsule fill content ranges from about 0.600 g to about 1.200 g.

107. The method according to claim 52, wherein the capsule fill content ranges from about 0.800 g to about 1.000 g.

108. The method according to claim 42, wherein the preconcentrate is administered twice per day.

109. The method according to claim 42, wherein the preconcentrate is administered three times per day.

110. The preconcentrate according to claim 56, wherein the fatty acid oil mixture comprises from about 40% to about 70% EPA and DHA, by weight of the fatty acid oil mixture.

111. The preconcentrate according to claim 56, wherein the fatty acid oil mixture comprises from about 40% to about 60% EPA and DHA, by weight of the fatty acid oil mixture.

112. The preconcentrate according to claim 56, wherein the fatty acid oil mixture comprises from about 40% to about 55% EPA and DHA, by weight of the fatty acid oil mixture.

113. The preconcentrate according to claim 56, wherein the fatty acid oil mixture comprises from about 50% to about 55% EPA and DHA, by weight of the fatty acid oil mixture.

114. The preconcentrate according to claim 56, wherein the EPA:DHA weight ratio of the fatty acid oil mixture ranges from about 1:6 to 6:1.

115. The preconcentrate according to claim 56, wherein the EPA:DHA weight ratio of the fatty acid oil mixture ranges from about 1:3 to 3:1.

116. The preconcentrate according to claim 56, wherein the EPA:DHA weight ratio of the fatty acid oil mixture ranges from about 1:2 to 1:3.

117. The preconcentrate according to claim 63, wherein the capsule fill content ranges from about 0.600 g to about 1.200 g.

118. The preconcentrate according to claim 63, wherein the capsule fill content ranges from about 0.800 g to about 1.000 g.

119. The preconcentrate according to claim 56, wherein the preconcentrate is a food supplement or nutritional supplement.

\* \* \* \* \*